(12) United States Patent
Crispino et al.

(10) Patent No.: US 7,432,373 B2
(45) Date of Patent: *Oct. 7, 2008

(54) PROCESSES AND INTERMEDIATES USEFUL FOR PREPARING FUSED HETEROCYCLIC KINASE INHIBITORS

(75) Inventors: Gerard Crispino, Lawrenceville, NJ (US); Stephanie Barbosa, Lambertville, NJ (US); Junying Fan, Monmouth Junction, NJ (US); Zhen-wei Cai, Belle Mead, NJ (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 369 days.

This patent is subject to a terminal disclaimer.

(21) Appl. No.: 11/165,875

(22) Filed: Jun. 24, 2005

(65) Prior Publication Data

US 2005/0288289 A1 Dec. 29, 2005

Related U.S. Application Data

(60) Provisional application No. 60/612,563, filed on Sep. 23, 2004, provisional application No. 60/583,459, filed on Jun. 28, 2004.

(51) Int. Cl.
C07D 487/04 (2006.01)
(52) U.S. Cl. .................................................... 544/183
(58) Field of Classification Search .................. 544/183
See application file for complete search history.

(56) References Cited

U.S. PATENT DOCUMENTS

| | | | |
|---|---|---|---|
| 3,646,202 A | 2/1972 | Mrozik | |
| 4,602,912 A | 7/1986 | de Sousa et al. | |
| 4,663,341 A | 5/1987 | Jacobson | |
| 4,753,940 A | 6/1988 | Sturm et al. | |
| 4,845,093 A | 7/1989 | Haga et al. | |
| 4,908,056 A | 3/1990 | Tseng | |
| 5,132,314 A | 7/1992 | Maienfisch et al. | |
| 5,135,949 A | 8/1992 | von der Saal et al. | |
| 5,646,176 A | 7/1997 | Golik et al. | |
| 6,022,884 A | 2/2000 | Mantlo et al. | |
| 6,143,743 A | 11/2000 | Wilde et al. | |
| 6,143,764 A | 11/2000 | Kubo et al. | |
| 6,214,344 B1 | 4/2001 | Schwall et al. | |
| 6,232,320 B1 | 5/2001 | Stewart et al. | |
| 6,262,094 B1 | 7/2001 | Hoefle et al. | |
| 6,355,660 B1 | 3/2002 | Ricks et al. | |
| 6,380,386 B2 | 4/2002 | Seitz et al. | |
| 6,521,622 B1 | 2/2003 | Ricks et al. | |
| 6,559,341 B2 | 5/2003 | Tohnishi et al. | |
| 6,603,044 B1 | 8/2003 | Tohnishi et al. | |
| 6,620,827 B2 | 9/2003 | De la Brouse-Elwood et al. | |
| 6,670,357 B2 | 12/2003 | Leftheris et al. | |
| 6,696,487 B2 | 2/2004 | Gerusz et al. | |
| 6,706,740 B2 | 3/2004 | Ricks et al. | |
| 6,750,246 B1 | 6/2004 | Kadow et al. | |
| 6,867,300 B2 | 3/2005 | Godfrey, Jr. et al. | |
| 6,869,952 B2 | 3/2005 | Bhide et al. | |
| 6,900,208 B2 | 5/2005 | Salvati et al. | |
| 6,933,386 B2 * | 8/2005 | Bhide et al. ................. | 544/183 |
| 6,951,859 B2 | 10/2005 | Bhide et al. | |
| 6,982,265 B1 | 1/2006 | Hunt et al. | |
| 7,030,112 B2 | 4/2006 | Salvati et al. | |
| 7,034,151 B2 | 4/2006 | Chen et al. | |
| 2001/0041673 A1 | 11/2001 | Fossa | |
| 2003/0082631 A1 | 5/2003 | Gustavsson et al. | |
| 2003/0232765 A1 | 12/2003 | Carter et al. | |
| 2003/0232831 A1 | 12/2003 | Dyckman et al. | |
| 2004/0044203 A1 | 3/2004 | Wittman et al. | |
| 2004/0048891 A1 | 3/2004 | Kato et al. | |
| 2004/0053908 A1 | 3/2004 | Funahashi et al. | |
| 2004/0072832 A1 | 4/2004 | Bhide et al. | |
| 2004/0082582 A1 | 4/2004 | Dyckman et al. | |
| 2004/0157846 A1 | 8/2004 | Chen et al. | |
| 2004/0209886 A1 | 10/2004 | Salvati et al. | |
| 2004/0229877 A1 | 11/2004 | Leftheris et al. | |
| 2004/0242603 A1 | 12/2004 | Fujiwara et al. | |
| 2005/0038035 A1 | 2/2005 | Takasugi et al. | |
| 2005/0043306 A1 | 2/2005 | Leftheris et al. | |
| 2005/0107462 A1 | 5/2005 | Godfrey, Jr. et al. | |
| 2005/0143398 A1 | 6/2005 | Das et al. | |
| 2005/0239820 A1 | 10/2005 | Borzilleri et al. | |
| 2005/0245530 A1 | 11/2005 | Borzilleri et al. | |
| 2005/0288290 A1 | 12/2005 | Borzilleri et al. | |
| 2006/0003967 A1 | 1/2006 | Shi et al. | |
| 2006/0004006 A1 | 1/2006 | Borzilleri et al. | |
| 2006/0030708 A1 | 2/2006 | Lobben | |

FOREIGN PATENT DOCUMENTS

| | | |
|---|---|---|
| AU | 200195986 | 4/2002 |
| DE | 31 39 457 | 4/1983 |
| DE | 197 10 609 | 9/1998 |
| EP | 0 151 962 | 8/1985 |
| EP | 0 119 774 | 6/1987 |
| EP | 0 152 910 | 7/1989 |
| EP | 0 919 542 | 6/1999 |
| EP | 1 243 582 | 9/2002 |
| EP | 1 411 046 | 4/2004 |
| GB | 2 106 500 | 4/1983 |
| JP | 54-115384 | 9/1979 |

(Continued)

OTHER PUBLICATIONS

Kempter, G. et al., "Synthesis of potential plant protective agents and pesticides from substituted anilines", Wissenschaftliche Zeitschrift, vol. 27, No. 1, pp. 101-120 (1983) (with English abstract).

(Continued)

*Primary Examiner*—Venkataraman Balasubram
(74) *Attorney, Agent, or Firm*—Elliott Korsen; Maureen S. Gibbons

(57) ABSTRACT

The present invention is directed to intermediates that are useful for preparing pyrrolotriazines, and processes for preparing such intermediates.

9 Claims, No Drawings

FOREIGN PATENT DOCUMENTS

| | | |
|---|---|---|
| JP | 57-51835 | 3/1982 |
| JP | 62-62 | 1/1987 |
| JP | 62-5959 | 1/1987 |
| JP | 62-5960 | 1/1987 |
| JP | 62-135463 | 6/1987 |
| JP | 2003-321472 | 11/2003 |
| SU | 1761753 | 9/1992 |
| WO | WO 97/17329 | 5/1997 |
| WO | WO 98/41513 | 9/1998 |
| WO | WO 99/01454 | 1/1999 |
| WO | WO 99/02514 | 1/1999 |
| WO | WO 99/24404 | 5/1999 |
| WO | WO 00/43366 | 7/2000 |
| WO | WO 00/50405 | 8/2000 |
| WO | WO 00/71129 | 11/2000 |
| WO | WO 00/75145 | 12/2000 |
| WO | WO 01/21576 | 3/2001 |
| WO | WO 01/21596 | 3/2001 |
| WO | WO 01/42243 | 6/2001 |
| WO | WO 01/47890 | 7/2001 |
| WO | WO 01/94353 | 12/2001 |
| WO | WO 02/32872 | 4/2002 |
| WO | WO 02/40486 | 5/2002 |
| WO | WO 02/44156 | 6/2002 |
| WO | WO 02/051397 | 7/2002 |
| WO | WO 02/085859 | 10/2002 |
| WO | WO 03/000194 | 1/2003 |
| WO | WO 03/000660 | 1/2003 |
| WO | WO 03/011028 | 2/2003 |
| WO | WO 03/033472 | 4/2003 |
| WO | WO 03/042172 | 5/2003 |
| WO | WO 03/082208 | 10/2003 |
| WO | WO 03/091229 | 11/2003 |
| WO | WO 03/099286 | 12/2003 |
| WO | WO 2004/001059 | 12/2003 |
| WO | WO 2004/002410 | 1/2004 |
| WO | WO 2004/009542 | 1/2004 |
| WO | WO 2004/032846 | 4/2004 |
| WO | WO 2004/048386 | 6/2004 |
| WO | WO 2004/054514 | 7/2004 |
| WO | WO 2004/058144 | 7/2004 |
| WO | WO 2004/060305 | 7/2004 |
| WO | WO 2005/005389 | 1/2005 |
| WO | WO 2005/021554 | 3/2005 |
| WO | WO 2005/026124 | 3/2005 |
| WO | WO 2005/030140 | 4/2005 |
| WO | WO 2005/042537 | 5/2005 |
| WO | WO 2005/058891 | 6/2005 |
| WO | WO 2005/082854 | 9/2005 |
| WO | WO 2005/082855 | 9/2005 |
| WO | WO 2005/097790 | 10/2005 |

OTHER PUBLICATIONS

Search Report "A", dated Jul. 2, 2003.
Dumas, J. et al., "Synthesis and Structure Activity Relationships of Novel Small Molecule Cathepsin D Inhibitors", Bioorganic & Medicinal Chemistry Letters, vol. 9, pp. 2531-2536 (1999).
Hunt, J.T. et al., "Discovery of the Pyrrolo[2,1-f][1,2,4]triazine Nucleus as a New Kinase Inhibitor Template", J. Med. Chem, vol. 47, No. 16, pp. 4054-4059 (2004).
Kurogi, Y. et al., "Discovery of Novel Mesangial Cell Proliferation Inhibitors Using a Three-Dimensional Database Searching Method", J. Med. Chem., vol. 44, No. 14, pp. 2304-2307 (2001).
Okada, H. et al., "Synthesis and Antitumor Activities of Novel Benzoylphenylurea Derivatives", Chem. Pharm. Bull., vol. 39, No. 9, pp. 2308-2315 (1991).
Xue, C.-B. et al., "Rational Design, Synthesis and Structure-Activity Relationships of a Cyclic Succinate Series of TNF-α Converting Enzyme Inhibitors. Part 2: Lead Optimization", Bioorganic & Medicinal Chemistry Letters, vol. 13, pp. 4299-4304 (2003).

U.S. Appl. No. 11/111,144, filed Apr. 21, 2005, Borzilleri et al.
U.S. Appl. No. 11/113,838, filed Apr. 25, 2005, Borzilleri et al.
U.S. Appl. No. 11/167,043, filed Jun. 24, 2005, Borzilleri et al.
U.S. Appl. No. 11/167,049, filed Jun. 24, 2005, Borzilleri et al.
Search Report "A", dated Dec. 16, 2004.
U.S. Appl. No. 09/573,829, filed May 18, 2000, Hunt et al.
U.S. Appl. No. 11/168,682, filed Jun. 28, 2005, Shi et al.
U.S. Appl. No. 11/197,970, filed Aug. 5, 2005, Lobben.
Bardelli, A. et al., "Concomitant activation of pathways downstream of Grb2 and PI 3-kinase is required for *Met*-mediated metastasis", Oncogene, vol. 18, pp. 1139-1146 (1999).
Barker, J.M. et al., "Thienopyridines. Part 7. Some Electrophilic Substitution Reactions of Thieno[2,3-*b*]- and -[3,2-*b*]pyridine Isosteres of 4-Oxygenated and 2,4-Dioxygenated Quinolines", J. Chem. Research (S), pp. 122-123 (1986).
Bottaro, D.P. et al., "Identification of the Hepatocyte Growth Factor Receptor as the c-*met* Proto-Oncogene Product", Science, vol. 251, pp. 802-804 (1991).
Bussolino, F. et al., "Hepatocyte Growth Factor Is a Potent Angiogenic Factor Which Stimulates Endothelial Cell Motility and Growth", The Journal of Cell Biology, vol. 119, No. 3, pp. 629-641 (1992).
Camp, R.L. et al., "*Met* Expression Is Associated with Poor Outcome in Patients with Axillary Lymph Node Negative Breast Carcinoma", Cancer, vol. 86, No. 11, pp. 2259-2265 (1999).
Christensen, J.G. et al., "A Selective Small Molecule Inhibitor of c-Met Kinase Inhibits c-Met-Dependent Phenotypes in Vitro and Exhibits Cytoreductive Antitumor Activity in Vivo", Cancer Research, vol. 63, pp. 7345-7355 (2003).
Cooper, C.S. et al., "Amplification and overexpression of the *met* gene in spontaneously transformed NIH3T3 mouse fibroblasts", The EMBO Journal, vol. 5, No. 10, pp. 2623-2628 (1986).
Di Renzo, M.F. et al., "Overexpression and Amplification of the Met/HGF Receptor Gene during the Progression of Colorectal Cancer", Clinical Cancer Research, vol. 1, pp. 147-154 (1995).
Dorn, H. et al., "Unambiguous Synthesis of 4,7-Dihydro-4-oxo-1H-pyrazolo[3,4-b]pyridine—Further Comments on the '(N-C)-Rearrangement' of (2-Alkoxycarbonyl-vinyl-amino)pyrazols", J. Prakt. Chem., vol. 324, No. 4, pp. 557-562 (1992).
Furge, K.A. et al., "Met receptor tryosine kinase: enhanced signaling through adapter proteins", Oncogene, vol. 19, pp. 5582-5589 (2000).
Gual, P., et al., "Sustained recruitment of phospholipase C-γ to Gab1 is required for HGF-induced branching tubulogenesis", Oncogene, vol. 19, pp. 1509-1518 (2000).
Hamdouchi, C. et al., "Imidazo[1,2-*b*]pyridazines, Novel Nucleus with Potent and Broad Spectrum Activity against Human Picornaviruses: Design, Synthesis, and Biological Evaluation", J. Med. Chem., vol. 46, No. 20, pp. 4333-4341 (2003).
Itoh, T. et al., "Studies on the Chemical Synthesis of Potential Antimetabolites. 30. Regioselective Introduction of a Chlorine Atom into the Imidazo[4,5-*b*]pyridine Nucleus", J. Heterocyclic Chem., vol. 19, pp. 513-517 (1982).
Jiang, W.G. et al., "Reduction of Stromal Fibroblast-induced Mammary Tumor Growth, by Retroviral Ribozyme Transgenes to Hepatocyte Growth Factor/Scatter Factor and its Receptor, c-MET", Clinical Cancer Research, vol. 9, pp. 4274-4281 (2003).
Kenworthy, P. et al., "The presence of scatter factor in patients with metastatic spread to the pleura", Br. J. Cancer, vol. 66, pp. 243-247 (1992).
Lai, J.-F. et al., "Involvement of Focal Adhesion Kinase in Hepatocyte Growth Factor-induced Scatter of Madin-Darby Canine Kidney Cells", The Journal of Biological Chemistry, vol. 275, No. 11, pp. 7474-7480 (2000).
Lee, J.-H. et al., "A novel germ line juxtamembrane *Met* mutation in human gastric cancer", Oncogene, vol. 19, pp. 4947-4953 (2000).
Lubensky, I.A. et al., "Hereditary and Sporadic Papillary Renal Carcinomas with c-*met* Mutations Share a Distinct Morphological Phenotype", American Journal of Pathology, vol. 155, No. 2, pp. 517-526 (1999).
Masuya, D. et al., "The tumour-stromal interaction between intratumoral c-Met and stromal hepatocyte growth factor associated with tumour growth and prognosis in non-small-cell lung cancer patients", British Journal of Cancer, vol. 90, pp. 1555-1562 (2004).

Matsumoto, K. et al., "Hepatocyte Growth Factor: Molecular Structure, Roles in Liver Regeneration, and Other Biological Functions", Critical Reviews in Oncogenesis, vol. 3, Nos. 1,2, pp. 27-54 (1992).

Montesano, R. et al., "Identification of a Fibroblast-Derived Epithelial Morphogen as Hepatocyte Growth Factor", Cell, vol. 67, pp. 901-908 (1991).

Park, M. et al., "Sequence of *MET* protooncogene cDNA has features characteristic of the tyrosine kinase family of growth-factor receptors", Proc. Natl. Acad. Sci. USA, vol. 84, pp. 6379-6383 (1987).

Quintela, J.M. et al., "A Ready One-pot Preparation for Pyrrolo[2,1-*f*][1,2,4]trianzine and Pyrazolo[5,1-*c*]pyrimido[4,5-*e*][1,2,4]triazine Derviatives", Tetrahedron, vol. 52, No. 8, pp. 3037-3048 (1996).

Rong, S. et al., "Met Expression and Sarcoma Tumorigenicity", Cancer Research, vol. 53, pp. 5355-5360 (1993).

Rong, S. et al., "Met Proto-oncogene Product Is Overexpressed in Tumors of p53-deficient Mice and Tumors of Li-Fraumeni Patients", Cancer Research, vol. 55, pp. 1963-1970 (1995).

Sachs, M. et al., "Essential Role of Gab1 for Signaling by the c-Met Receptor In Vivo", The Journal of Cell Biololgy, vol. 150, No. 6, pp. 1375-1384 (2000).

Sanghvi, Y.S. et al., "Synthesis and Biological Evaluation of Certain C-4 Substituted Pyrazolo[3,4-*b*]pyridine Nucleosides", J. Med. Chem., vol. 32, No. 5, pp. 945-951 (1989).

Scarpino, S. et al., "Hepatocyte Growth Factor (HGF) Stimulates Tumour Invasiveness in Papillary Carcinoma of the Thyroid", Journal of Pathology, vol. 189, pp. 570-575 (1999).

Schaeper, U. et al., "Coupling of Gab1 to c-Met, Grb2, and Shp2 Mediates Biological Responses", The Journal of Cell Biology, vol. 149, No. 7, pp. 1419-1432 (2000).

Soman, N.R. et al., "The *TPR-MET* oncogenic rearrangement is present and expressed in human gastric carcinoma and precursor lesions", Proc. Natl. Acad. Sci. USA, vol. 88, pp. 4892-4896 (1991).

Sonnenberg, E. et al., "Scatter Factor/Hepatocyte Growth Factor and Its Receptor, the c-met Tyrosine kinase, Can Mediate a Signal Exchange between Mesenchyme and Epithelia during Mouse Development", The Journal of Cell Biology, vol. 123, No. 1, pp. 223-235 (1993).

Stabile, L.P. et al., "Inhibition of human non-small cell lung tumors by a c-Met antisense/U6 expression plasmid strategy", Gene Therapy, vol. 11, pp. 325-335 (2004).

Stella, M.C. et al., "HGF: a multifunctional growth factor controlling cell scattering", The International Journal of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K.A. et al., "Hepatocyte growth factor/scatter factor-induced intracellular signalling", International Journal of Experimental Pathology, vol. 81, pp. 17-30 (2000).

Takayama, H. et al., "Diverse tumorigenesis associated with aberrant development in mice overexpressing hepatocyte growth factor/scatter factor", Proc. Natl. Acad. Sci. USA, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Tedder, M.E. et al., "Structure-based design, synthesis, and antimicrobial activity of purine derived SAH/MTA nucleosidase inhibitors", Bioorganic & Medicinal Chemistry Letters, vol. 14, pp. 3165-3168 (2004).

Temple, Jr., C. et al., "Preparation and Properties of Some Isomeric *v*-Triazolopyridines. 1- and 3-Deaza-8-azapurines", J. Org. Chem., vol. 37, No. 23, pp. 3601-3604 (1972).

Thibault, C. et al., "Concise and Efficient Synthesis of 4-Fluoro-1*H*-pyrrolo[2,3-*b*]pyridine", Organic Letters, vol. 5, No. 26, pp. 5023-5025 (2003).

Zhang, Z. et al., "A General Method for the Preparation of 4- and 6-Azaindoles", J. Org. Chem., vol. 67, pp. 2345-2347 (2002).

Bryant, R.D. et al., "A Large Scale Synthesis of 3-Chloro-5-methoxypyridazine", J. Heterocyclic Chem., vol. 32, pp. 1473-1476 (1995).

Burckhalter, J.H. et al., "Aminoalkylphenols as Antimalarials, II. (Heterocyclic-amino)-α-amino-*o*cresols. The Synthesis of Camoquin", J. Am. Chem. Soc., vol. 70, pp. 1363-1373 (1948).

Cañibano, V. et al., "Mild Regioselective Halogenation of Activated Pyridines with *N*-Bromosuccinimide", Synthesis, vol. 14, pp. 2175-2179 (2001).

Cheng, C.-C. et al., "Comprehensive Studies on Dual Excitation Behavior of Double Proton versus Charge Transfer in 4-(*N*-Substituted amino)-1H-pyrrolo'2,3-*b*'pyridines", J. Phys. Chem. A, vol. 107, No. 10, pp. 1459-1471 (2003).

Cheng, C.C. et al., "Potential Purine Antagonists. XII. Synthesis of 1-Alkyl(aryl)-4,6-disubstituted Pyrazolo'3,4-*d*'pyrimidines", J. Org. Chem., vol. 23, pp. 852-861 (1958).

Chi, S.-M. et al., "Palladium-catalyzed functionalization of 5- and 7-azaindoles", Tetrahedron Letters, vol. 41, pp. 919-922 (2000).

Chung, H.-A. et al., "Direct Functionalization of 4,5-Dichloropyridazin-6-one", J. Heterocyclic Chem., vol. 36, pp. 905-910 (1999).

Frey, L.F. et al., "Practical routes toward the synthesis of 2-halo- and 2-alkylamino-4-pyridinecarboxaldehydes", Tetrahedron Letters, vol. 42, pp. 6815-6818 (2001).

Gemma, S. et al., "Polycondensed heterocycles. Part 12: An approach to the synthesis of 2-acetyl-1'-methyl-1,2,3,4-tetrahydrospiro-[isoquinoline-1,4'-pyrrolidine]-2'-one", Tetrahedron, vol. 58, pp. 3689-3692 (2002).

Gero, T.W. et al., "Halogenation of 2-Hydroxynicotinic Acid", Synthetic Communications, vol. 19, Nos. 3&4, pp. 553-559 (1989).

Girgis, N.S. et al., "The Synthesis of 5-Azaindoles by Substitution-Rearrangement of 7-Azaindoles upon Treatment with Certain Primary Amines", J. Heterocyclic Chem., vol. 26, pp. 317-325 (1989).

Greene, T.W. et al., Protective Groups in Organic Synthesis, 2nd Ed., John Wiley & Sons, Inc., publ., pp. ix-x (table of contents) (1991).

Kirk, K.L., "Synthesis of Ring-Fluorinated Serotonins and Melatonins", J. Heterocyclic Chem., vol. 13, pp. 1253-1256 (1976).

Kitamura, C. et al., "Synthesis and reactions of 3,3'-dibromodihydrodipyrrins", J. Chem. Soc. Perkin Trans. 1, pp. 1443-1447 (1997).

Koch, V. et al., "Chemistry of 3-Hydroxypyridine Part 2: Synthesis of 5,6-Dihalo-3-hydroxypyridines", Synthesis, pp. 499-501 (1990).

Morrill, C. et al., "Synthesis of Functionalized Vinyl Boronates via Ruthenium-Catalyzed Olefin Cross-Metathesis and Subsequent Conversion to Vinyl Halides", J. Org. Chem., vol. 68, No. 15, pp. 6031-6034 (2003).

Nicolaou, I. et al., "[1-(3,5-Difluoro-4-hydroxyphenyl)-1*H*pyrrol-3-yl]phenylmethanone as a Bioisostere of a Carboxylic Acid Aldose Reductase Inhibitor", J. Med. Chem., vol. 47, No. 10, pp. 2706-2709 (2004).

Schaus, J.M. et al., "Synthesis and Structure-Activity Relationships of Potent and Orally Active 5-HT$_4$ Receptor Antagonists: Indazole and Benzimidazolone Derivatives", J. Med. Chem., vol. 41, No. 11, pp. 1943-1955 (1998).

Tabanella, S. et al., "Preparation of enantiomerically pure pyridyl amino acids from serine", Org. Biomol. Chem., vol. 1, pp. 4254-4261 (2003).

U.S. Appl. No. 11/292,358, filed Dec. 1, 2005, Borzilleri et al.

Database Crossfire Beilstein Beilstein Institut Zur Foerderung Der Chemischen Wissenschaft, Frankfurt Am Main, DE; XP002362294 Database accession No. BRN 667921.

Database Crossfire Beilstein Beilstein Institut Zur Foerderung Der Chemischen Wissenschaft, Frankfurt Am Main, DE; XP002362295 Database accession No. BRN 413351.

Database Crossfire Beilstein Beilstein Institut Zur Foerderung Der Chemischen Wissenschaft, Frankfurt Am Main, DE; XP002362296 Database accession No. BRN 450834.

Database Crosssfire Beilstein Beilstein Institut Zur Foerderung Der Chemischen Wissenschaft, Frankfurt Am Main, DE; XP002362297 Database accession No. BRN 448780.

"Hepatocyte growth factor/scatter factor, Met and cancer references", Van Andel Institute, http://www.vai.org/vari/metandcancer/ (as revised Oct. 4, 2005).

U.S. Appl. No. 11/406,795, filed Apr. 19, 2006, Borzilleri et al.

* cited by examiner

PROCESSES AND INTERMEDIATES USEFUL FOR PREPARING FUSED HETEROCYCLIC KINASE INHIBITORS

RELATED APPLICATIONS

This application claims priority benefit under Title 35 § 119(e) of U.S. Provisional Application Nos. 60/583,459, filed Jun. 28, 2004, and 60/612,563, filed Sep. 23, 2004, the contents of which are herein incorporated by reference.

FIELD OF INVENTION

This invention relates to intermediates and processes for preparing intermediates that are useful in the manufacture of pyrrolotriazines. Pyrrolotriazines have been found to be useful in the treatment of cancer by inhibiting protein tyrosine kinase activity. The pharmaceutical compositions that comprise these compounds are also useful in the treatment of diseases, other than cancer, which are associated with signal transduction pathways operating through growth factor and anti-angiogenesis receptors such as c-Met.

BACKGROUND

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54,1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65,1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-55, 2003; Lee et al., *Oncogene*, 19:4947-53, 2000 and Direnzo et al., *Clin. Cancer Res.*, 1: 147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res*. 55:1963-1970, 1995; Rong et al., *Cancer Res*. 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer*, 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS*, 94:701-6, 1997) and an amplified/overexpressed Met spontaneously transforms NIH-3T3 cells (Cooper et al., *EMBO J.*, 5:2623-8, 1986).

Biological agents, such as ribozymes, antibodies and antisense RNA targeting either HGF or Met have been shown to inhibit tumorogenesis (Stabile et al., *Gene Therapy*, 11:325-35, 2004, Jiang et al., *Clin. Cancer Res*, 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY

The present invention is directed to processes for preparing pyrrolotriazine compounds that are useful in the treatment of cancer.

In one embodiment of the present invention, a process for making a compound having the formula V is provided:

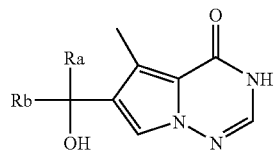

V wherein $R^a$ and $R^b$ are alkyl, comprising the steps of contacting a compound having the formula:

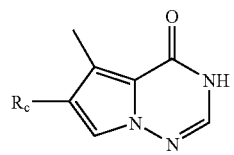

wherein $R^c$ is $C(O)_2R^e$ wherein $R^e$ is alkyl or substituted alkyl, such as methyl, ethyl, butyl, t-butyl, or benzyl with an alkyl organometallic agent such as a Grignard reagent or an organolitihium reagent for a time and under conditions sufficient to produce Compound V. In some preferred embodiments, the organometallic agent is methyl magnesium chloride, methyl magnesium bromide, ethyl magnesium chloride, ethyl magnesium bromide, methyl magnesium iodide, ethyl magnesium iodide, methyllithium or ethyllithium.

According to another embodiment of the present invention, a process is provided for making a compound having the formula VI:

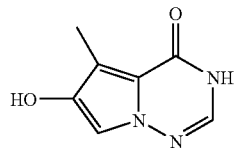

VI comprising contacting a compound having formula V

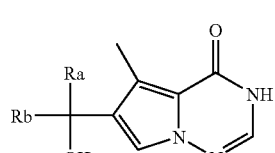

V wherein $R_a$ and $R_b$ are alkyl, with an acid, such as an organic acid, a mineral acid, a Lewis acid, or an acidic ion exchange resin, in the presence of a peroxide for a time and under conditions sufficient to produce compound VI, and may further include the step of quenching the reaction with the addition of a reducing agent, such as sodium metabisulfite, sodium hydrogen sulfite, sodium thiosulfate, or sodium hydrogen sulfite.

In some embodiments of the present invention, the acid is selected from the group consisting of p-toluene sulfonic acid, methanesulfonic acid, $BF_3$-OEt, trifluoroacetic acid, formic acid, sulfuric acid, nitric acid, an acidic zeolite, and an acidic ion exchange resin.

In one embodiment of the present invention, a process is provided for preparing a compound of formula VII:

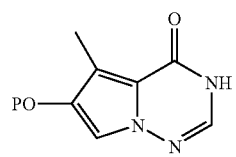

VII wherein P is a protecting group, comprising the step of contacting a compound having formula VI:

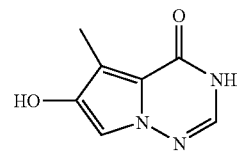

VI with an acylating agent, such as formic acid, acetyl chloride, acetic anhydride, pivaloyl chloride, pivalic anhydride, benzoyl chloride, di-t-butyl dicarbonate or an alkylating agent such as methyl iodide, methyl bromide, dimethylsulfate, dimethyl carbonate, chloromethylmethyl ether, 3,4-dihydro-2H-pyran, benzyl chloride, benzyl bromide, 4-methoxybenzylchloride, or 4-methoxybenzyl bromide for a time and under conditions sufficient to effect an acylation or an alkylation reaction that yields compound VII.

According to another embodiment of the present invention, a process is provided for preparing a compound having the formula X:

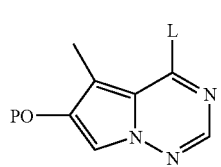

X wherein L is a leaving group and P is a protecting group comprising the steps of: contacting a compound having the formula VII:

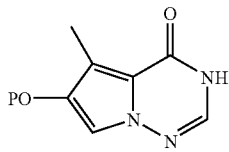

with an agent, such as phenylphosphonic dichloride, thionyl chloride, phosphorus oxybromide, trifluoromethanesulfonic anhydride, phosphorus oxychloride, phosphorus pentachloride, or a mixture of phosphorus oxychloride and phosphorus pentachloride, for a time and under conditions sufficient to afford compound X.

In one embodiment of the present invention, a process for preparing a compound having the formula IX is provided:

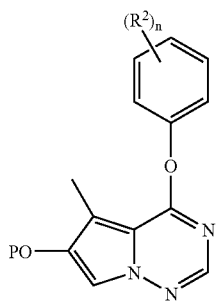

wherein $R^2$ is H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, aryalkyl, substituted arylalkyl, heterocycloalkyl, or substituted heterocycloalkyl; and $R^5$, R and $R^7$ are H, alkyl, cycloalkyl, aryl, or heteroaryl comprising the step of contacting a compound having formula VII:

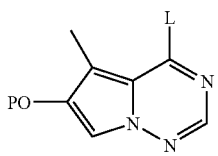

wherein P is a protecting group and L is a leaving group, with a substituted phenol for a time under conditions sufficient to form the compound IX.

DESCRIPTION

The present invention is directed to processes and intermediates that are useful for making pyrrolotriazine compounds. Pyrrolotriazine compounds have been found to be useful in the treatment of cancer. See, for example, U.S. patent application Ser. No. 09/573829 and U.S. patent application Ser. No. 60/612,563, filed Sep. 23, 2004 the disclosures of which are herein incorporated by reference in their entirety.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine, The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups such as amino, alkylamino, etc.

The numbers in the subscript after the symbol "C" define the number of carbon atoms a particular group can contain. For example "$C_1$ to $C_6$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_1$ to $C_6$ alkyl" can also refer to $C_1$ to $C_6$ alkylene which bridges two groups; examples include propane-1,3-diyl, butane-1,4-diyl, 2-methyl-butane-1,4-diyl, etc. "$C_2$ to $C_6$ alkyenyl means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_2$ to $C_6$ alkenyl" can also refer to $C_2$ to $C_6$ alkenediyl which bridges two groups; examples include ethylene-1,2-diyl (vinylene), 2-methyl-2-butene-1,4-diyl, 2-hexene-1,6-diyl, etc. "$C_2$ to $C_6$ alkynyl" means a straight or branched carbon chain having at least one carbon-carbon triple bond, and from two to six carbon atoms; examples include ethynyl, propynyl, butynyl, and hexynyl.

The terms "alkoxy" or "alkylthio" herein alone or as part of another group denote an alkyl group as described above bonded through an oxygen linkage (—O—) or a sulfur linkage (—S—), respectively.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group or —C(O)R.

The term "alkylcarbonyloxy" herein alone or as part of another group denotes an alkylcarbonyl group bonded through an oxygen linkage.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, such as Br, F, or Cl, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=O, 1, 2), or thiol.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl. carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$CO_2H$, —C(=O)H, —$CO_2$-alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The term "heterocycloalkyl" herein alone or as part of another group refers to a stable, saturated, or partially unsaturated monocyclic ring system containing 5 to 7 ring members of carbon atoms and other atoms selected from nitrogen, sulfur and/or oxygen. A heterocyclic ring may be a 5, 6 or 7-membered monocyclic ring and contain one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocycloalkyl groups include piperazine, piperidine, morpholine, homomorpholine, thiomorpholine, pyrrolidine, and azetidine.

A heteroaryl or heterocycloalkyl group may also be an 8-11 membered bicyclic ring which consists of carbon atoms and contains one, two, or three heteroatoms selected from nitrogen, oxygen and/or sulfur. Some preferred bicyclic rings include benzodioxole, quinoxaline, indolyl, and quinolinyl. The term "optionally substituted" as it refers to "heteraryl" or heterocycloalkyl herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

In a preferred embodiment of the present invention, processes and intermediates are provided for preparing compounds having Formulas I and II:

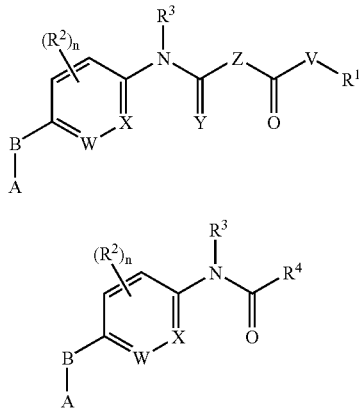

including pharmaceutically acceptable salts thereof, wherein:

$R^1$ is H, alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclo, substituted heterocyclo, heteroarylalkyl, substituted heteroarylalkyl, heterocycloalkyl, or substituted heterocycloalkyl;

each $R^2$ is independently, H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, aryalkyl, substituted arylalkyl, heterocycloalkyl, or substituted heterocycloalkyl;

B is O, $NR^8$, S, SO, $SO_2$, $CR^9R^{10}$;
V is $NR^{11}$ or $-(CR^{47}R^{48})_p-$;
W or X are independently C or N;
Y is O, S, or $NR^{12}$;
Z is $-CR^{13}R^{14}-$, $-(CR^{13}R^{14})_m NR^{15}-$;
l is 0 to 4;
m is 0 to 2;
n is 0 to 4;
p is 0 to 4, provided that if p is 0, $R^1$ is not phenyl;
A is:

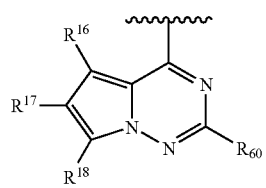

$R^3$, $R^5$, $R^6$, $R^7$, $R^8$, $R^{11}$ and $R^{15}$ are each independently H, alkyl, substituted alkyl, cycloalkyl, substituted cycloalkyl, aryl, substituted aryl, heteroaryl, substituted heteroaryl, heterocycloalkyl, or substituted heterocycloalkyl;

$R^4$ is aryl, substituted aryl, heteroaryl, substituted heteroaryl, heterocycloalkyl, or substituted heterocycloalkyl;

$R^9$ and $R^{10}$ are independently H, halogen, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{12}$ is H, alkyl, substituted alkyl, CN, $NO_2$ or $SO_2NH_2$;

$R^{13}$, $R^{14}$, $R^{15}$, $R^{47}$ and $R^{48}$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form a carbocyclic or heterocyclic ring of 3 to 8 atoms;

$R^{16}$, $R^{17}$, $R^{18}$, and $R^{60}$ are independently H, halogen, $NO_2$, cyano, $OR^{26}$, $NR^{27}R^{28}$, $CO_2R^{29}$, $C(O)NR^{30}NR^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, $-CO(CH_2)_l R^{41}$; $-CONH(CH_2)_l R^{42}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

Certain compounds of Formulas I and II may generally be prepared according to the following Schemes. The compounds are synthesized readily using synthetic methods known to one skilled in the art. Tautomers and solvates (e.g., hydrates) of the compounds of Formulas I and II are also within the scope of the present invention. Methods of solvation are generally known in the art. Accordingly, the compounds of the instant invention may be in the free or hydrate form, and may be obtained by methods exemplified by the following schemes below.

In general, the desired fused heterocycles can be prepared using the synthetic routes outlined in Schemes 1-3. The leaving group (Lg), such as a halogen (or triflate) of a heterocycle (A, whereby open positions may be optionally substituted) 1 can be displaced with a substituted phenol 2 to provide ether 3 (Scheme 1). Groups A-Lg can be prepared according to the general procedures outlined in, for example, Hunt, J. T. et al. WO 00/071129; Hunt, J. T. et al. *J. Med. Chem.* 2004, 47, 4054-4059; Leftheris, K. et al. WO 02/040486; Mastalerz, H. et al. WO 03/042172; Dyckman, A. et al. WO 03/091229; Vite, G. D. et al. WO 04/054514; Salvati, M. E. et al. WO 03/082208; Thibault, C. et al. *Org. Lett.* 2003, 5, 5023-5025; Zhang, Z. et al. *J. Org. Chem.* 2002, 67, 2345-2347; Itoh, T. et al. *J. Heterocyclic Chem.* 1982, 19, 513-517; Tedder, M. E. et al. *Bioorg. Med. Chem. Lett.* 2004, 14, 3165-3168; Dorn, H. et al. *J. Prakt. Chem.* 1982, 324, 557; Sanghvi, Y. S. et al. *J. Med. Chem.* 1989, 32, 945-951; Temple, C. Jr. et al. *J. Org. Chem.* 1972, 37, 3601-3604; Hurst, J. et al. EP119774; Hurst, J. et al. EP151962; Ward, R. W. et al. EP152910; Luzzio, M. J. et al. WO 01/094353; Marx, M. A. et al. WO 03/000194; Boschelli, D. H. et al. WO 04/048386; He, M. et al. WO 05/021554; Barker, J. M. et al. *J. Chem. Res., Synopses* 1986, 4, 122-123, the disclosures of which are herein incorporated by reference. Reduction of the nitro group of intermediate 3 with, for example either zinc dust and ammonium chloride or Adam's catalyst (platinum(IV) oxide) under catalytic hydrogenation conditions can furnish the aniline 4. Treatment of the aniline 4 with an isocyanate 5 (X=O) or isothiocyanate 5 (X=S) affords the desired acylurea or acylthiourea 6, respectively.

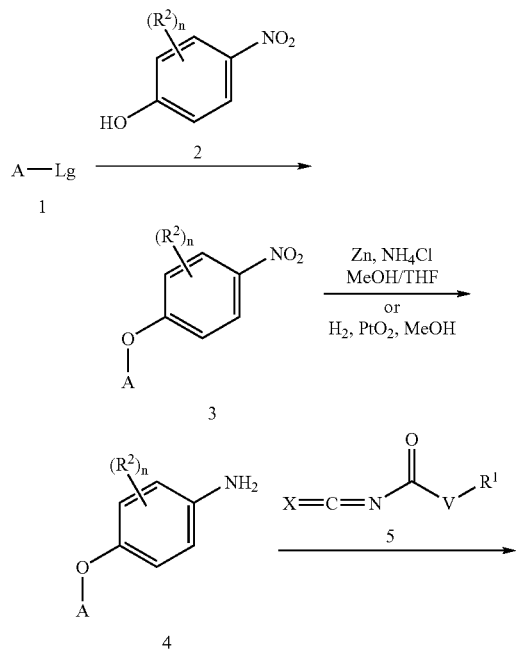

SCHEME 1

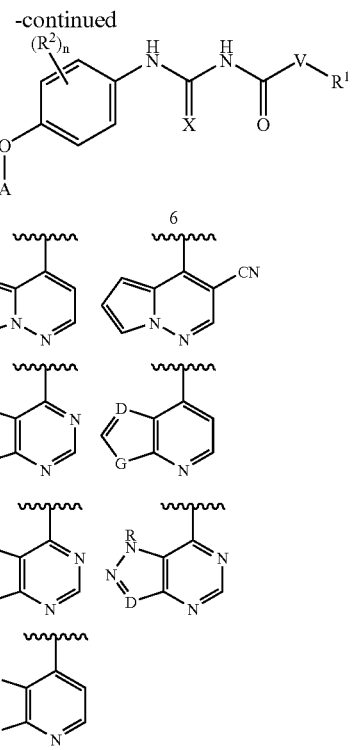

Lg=leaving group, such as a halogen
X=O or S
G is O, S, or $NR^{21}$
D is $CR^{20}$ or N
V=as defined above Alternatively, the appropriately substituted aniline 7 can be treated with an isocyanate 5 (X=O) or isothiocyanate 5 (X=S) to give the phenol 8 (Scheme 2). Reaction of intermediate 8 with a heterocycle (A-Lg) 1 can provide the desired compound 6.

SCHEME 2

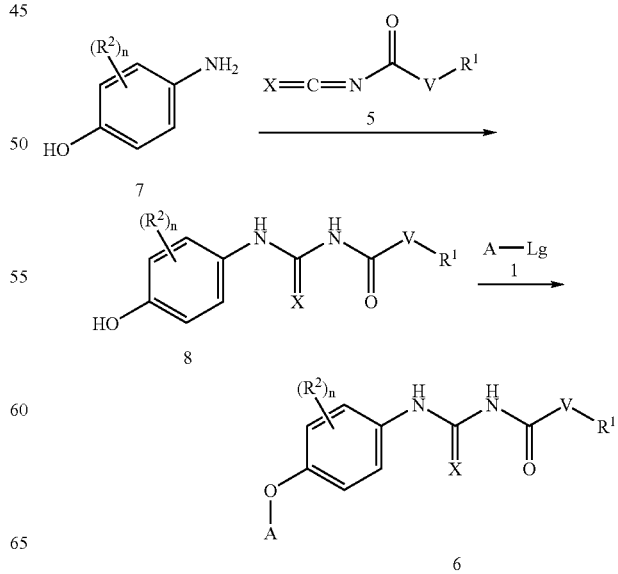

A = 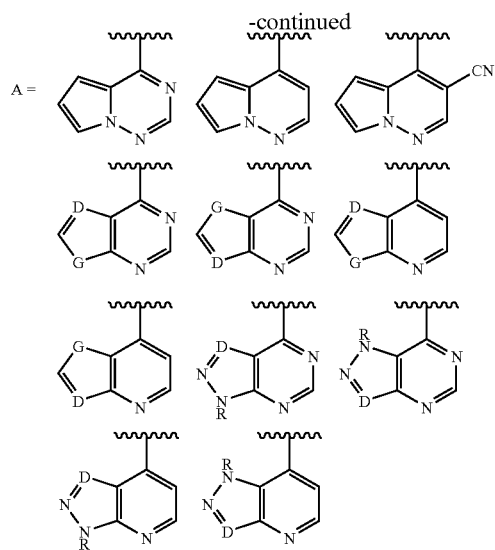

Lg=leaving group, such as a halogen
X=O or S
G is O, S, or NR[21]
D is CR[20] or N
V=as defined above In general, amide derivatives described in the invention can be prepared using the chemistry outlined in Scheme 3. For example, aniline 9 (derived from Scheme 1) can be acylated with compound 10 to provide amide 11. Hydrolysis of the ester 11 with, for example sodium hydroxide can afford carboxylic acid 12. Desired compound 13 can then be obtained from intermediate 12 using known amide-bond forming conditions. Alternatively, aniline 9 can be converted directly to compound 13 using carboxylic acid 14 and a coupling agent, such as benzotriazol-1-yloxytris(trimethylamino)phosphonium hexafluorophosphate, 1-(dimethylaminopropyl)-3-ethylcarbodiimide hydrochloride, or bromotripyrrolidinophosphonium hexafluorophosphate. Treatment of aniline 9 with an acid chloride 15 (X=Cl) or a carboxylic acid 15 (X=OH) and a coupling reagent can provide amides of the type 16.

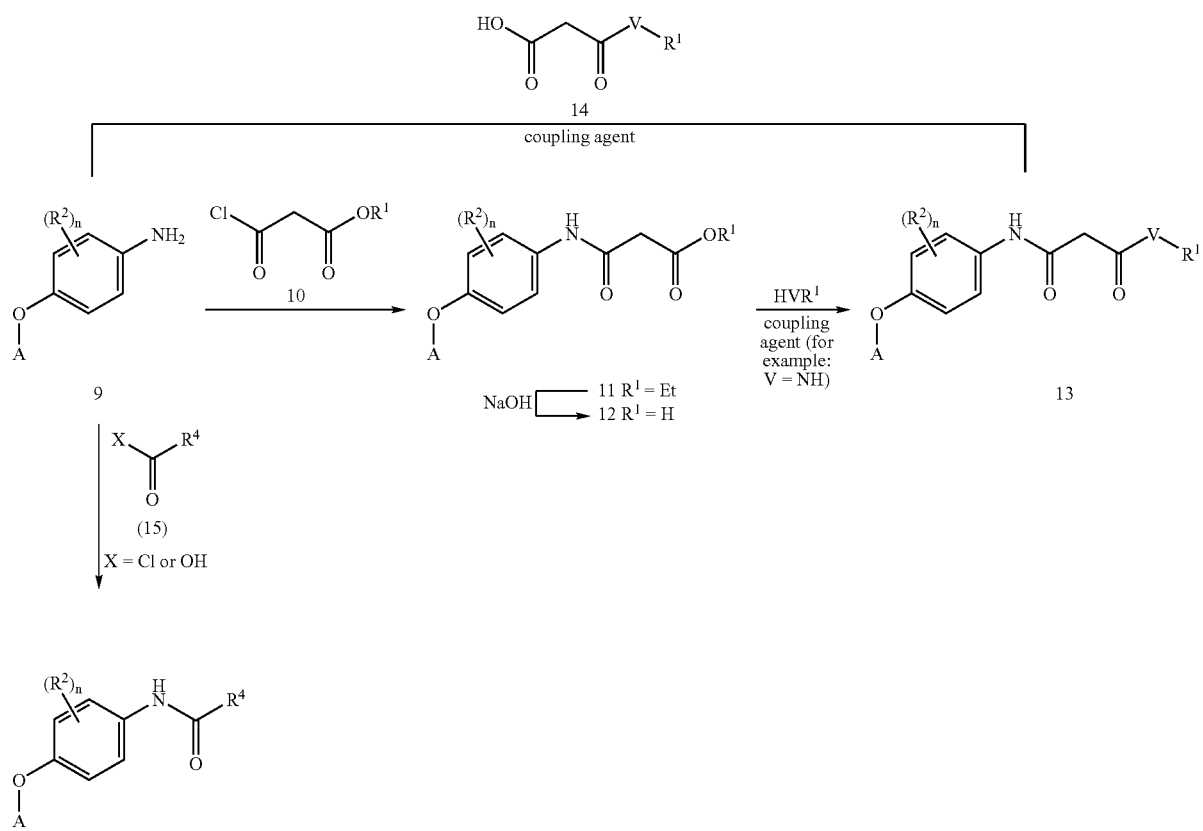

-continued

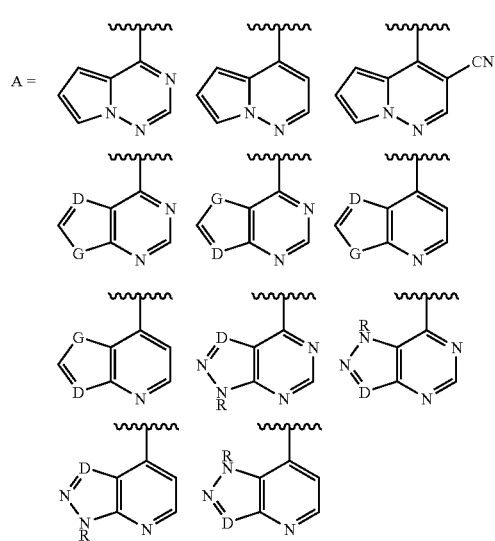

G is O, S, or NR[21]
D is CR[20] or N
V=as defined above

A substituted heterocyclic derivative, for example pyrrolotriazine compound 26a/b (Scheme 5), can be prepared using the synthetic routes outlined in Schemes 4 and 5. Carboxylic esters, wherein R can be an alkyl or an aryl (such as phenyl) 17 can be contacted with no less than 2 equivalents of an alkyl or aryl organometallic agent such as a Grignard reagent, organolithium, organozinc, etc. to produce the tertiary alcohol 18 (Scheme 4). The reaction is generally performed in an ether solvent, such as tetrahydrofuran, dibutylether, or diethyl ether, or any other non-reactive solvent such as benzene, toluene, or hexane, for example. Tertiary alcohol 18 can be treated with a mixture of acid in the presence of hydrogen peroxide or organic peroxides such as t-butylhydroperoxide, cumenehydroperoxide to affect the rearrangement to hydroxypyrrolotriazine 19. Almost any acid could be used as the catalyst for the oxidative rearrangement, the reaction has been demonstrated with organic acids, mineral acids, and Lewis acids. Some acids which have been used for this type of reaction include: p-toluenesulfonic acid, methansulfonic acid, formic acid, sulfuric acid, nitric acid, $BF_3$- $OEt_2$, trifluoroacetic acid, acidic zeolites, and acidic ion exchange resins. The concentration of the acid can be varied, the concentration and strength of the acid is used to control the kinetics of the reaction. The concentration of the peroxide can be varied from 30-50%. Any reducing agent which reacts to decompose hydrogen peroxide could be used in the quenching of this reaction, including, but not limited to sodium metabisulfite, sodium hydrogen sulfite, sodium thiosulfate, sodium hydrosulfite. A variety of bases can be used while quenching the reaction to control the pH. Hydroxypyrrolotriazine 19 can be reacted with a variety of acylating reagents, to furnish 20 (where, for example, P can be pivalate ester). Compound 20 can be contacted with an appropriate halogenating agent (for example, phosphorous oxychloride, $POCl_3$) to afford 21 (L=Cl). Other reagents can be used to accomplish this transformation besides $POCl_3$, including $PCl_5$, mixtures of $PCl_5/POCl_3$, $PhP(O)Cl_2$, $SOCl_2$. Usually an amine is used to catalyze the reaction, including $Et_3N$, $PhNMe_2$, DABCO, etc. Additionally, formamides such as, for example N,N-dimethylformamide and alkylamides such as N-methylpyrrolidinone can also be used to catalyze the reaction. The reaction can be run in any solvent inert to the haloginating agent, including benzene, toluene, THF, etc.

SCHEME 4

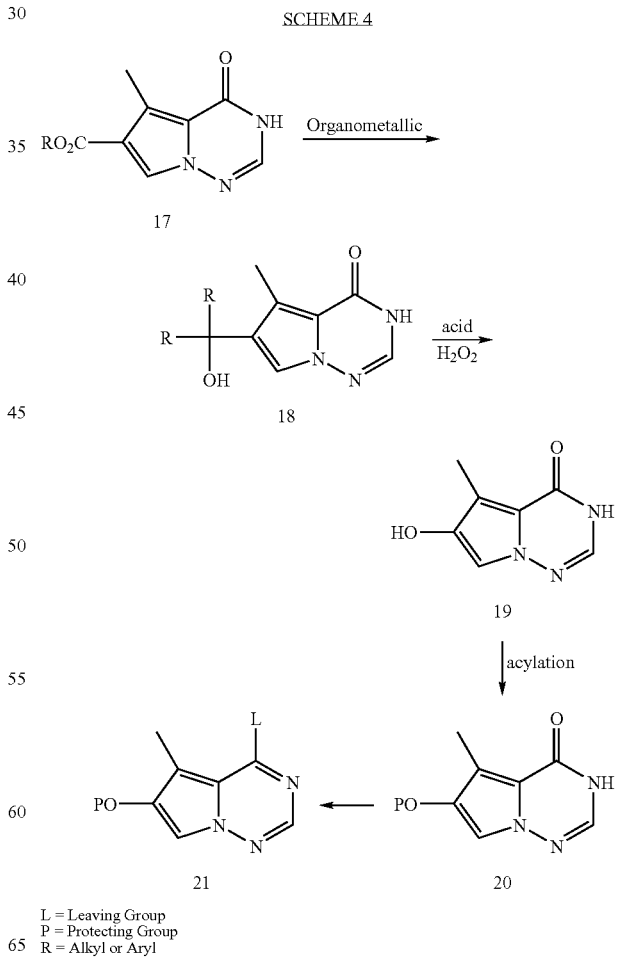

L = Leaving Group
P = Protecting Group
R = Alkyl or Aryl

The appropriately protected imidate 21 (Scheme 5) can be treated with an optionally substituted phenol 2 to provide intermediate 22. Phenol 23, derived from deprotection of compound 22 (using sodium hydroxide in the case where P=pivalate) can be converted to ether 24 via a Mitsunobu reaction with an alcohol. Reduction of the nitro substituent of 24 using the same conditions described above in Scheme 1 can furnish the aniline 25. Conversion of aniline 25 to the desired acylurea, acylthiourea or amide 26a/b can be accomplished using chemistry previously described in Schemes 1 and 3.

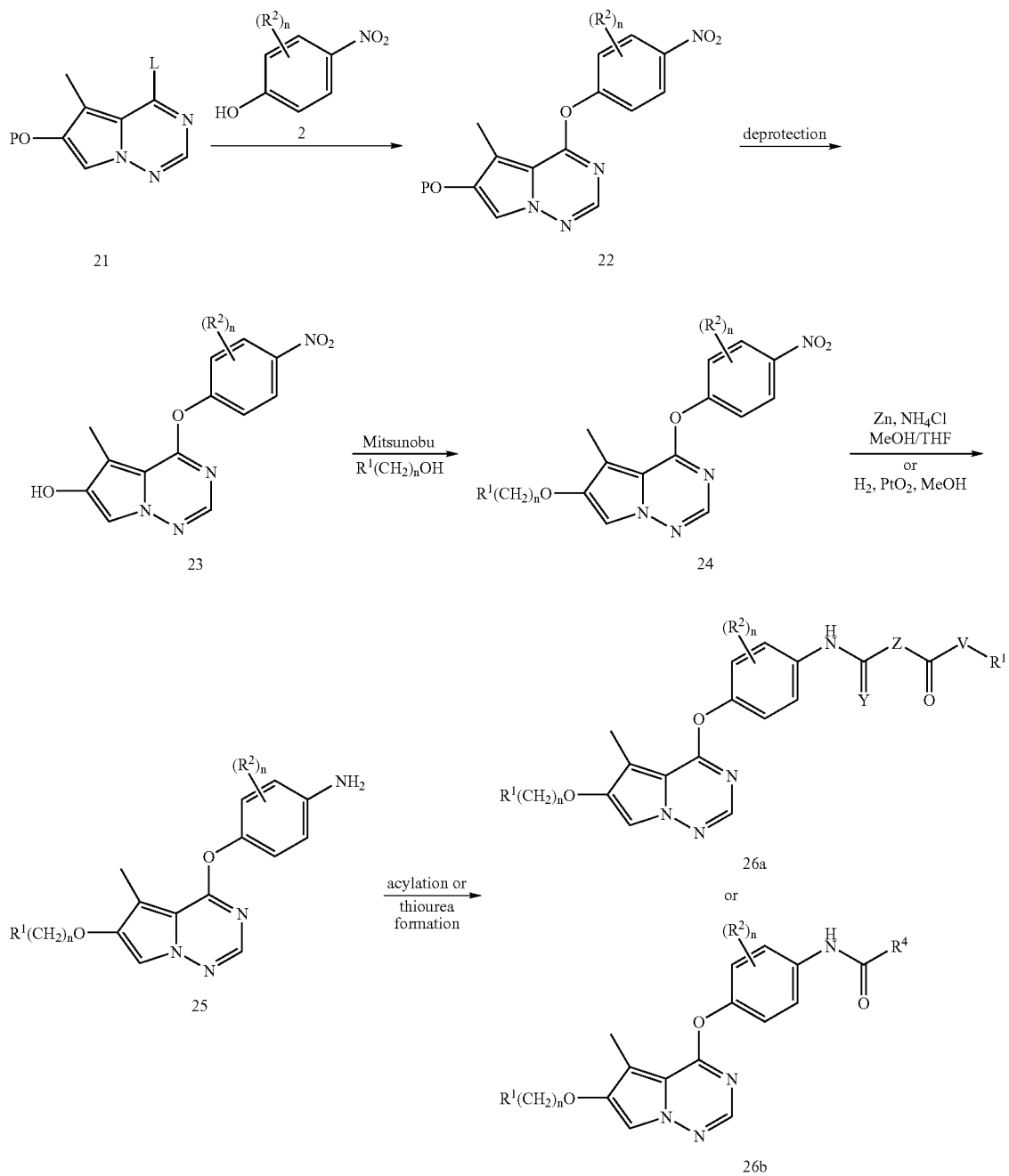

$R^1(CH_2)_nOH$ = any alcohol, but for example:
n = 2–4
$R^1$ = $N(CH_3)_2$, morpholine, N—Me piperazine, etc Amine compounds 30 can be prepared using the chemistry described in Scheme 6. Reduction of ester 27 with for example, diisobutylaluminum hydride (DIBAL-H) can provide alcohol 28. Oxidation of compound 28 with for example Dess-Martin periodinane (1,1,1-tris(acetyloxy)-1,1-dihydro-1,2-benziodoxol-3-(1H)-one) can afford aldehyde 29. Reductive amination of aldehyde 29 with an appropriately substituted amine in the presence of a reducing agent, such as sodium triacetoxyborohydride can furnish the desired amine 30.

SCHEME 6

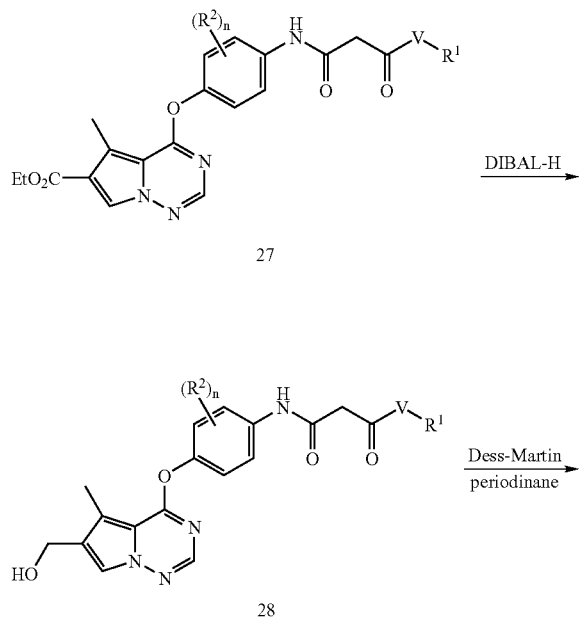

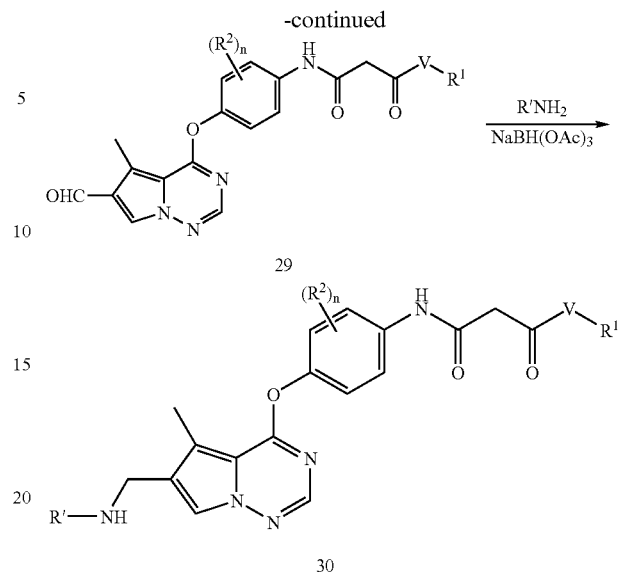

Various substituents, such as optionally substituted aryl, heteroaryl or vinyl groups can be introduced onto the 5-position of the pyrrolo[2,1-f][1,2,4]triazine ring using the chemistry outlined in Scheme 7. The aminopyrrole derivative 31 can be cyclized in the presence of formamide to produce 5-chloropyrrolo[2,1-f][1,2,4]triazin-4(3H)-one (32). Treatment of intermediate 32 with $POCl_3$ in the presence of a base, such as Hunig's base at elevated temperatures can afford 4,5-dichloropyrrolo[2,1-f][1,2,4]triazine (33). The coupling of an appropriately substituted phenol 2 with compound 33 in the presence of a base, such as potassium carbonate can provide intermediate 34. The nitro group of 34 can be reduced using zinc dust and ammonium chloride to generate the aniline 35. Palladium-mediated coupling reactions with various boronic acids can provide intermediate 36, which can be converted to the desired compounds 37 or 38 using chemistry described above.

SCHEME 7

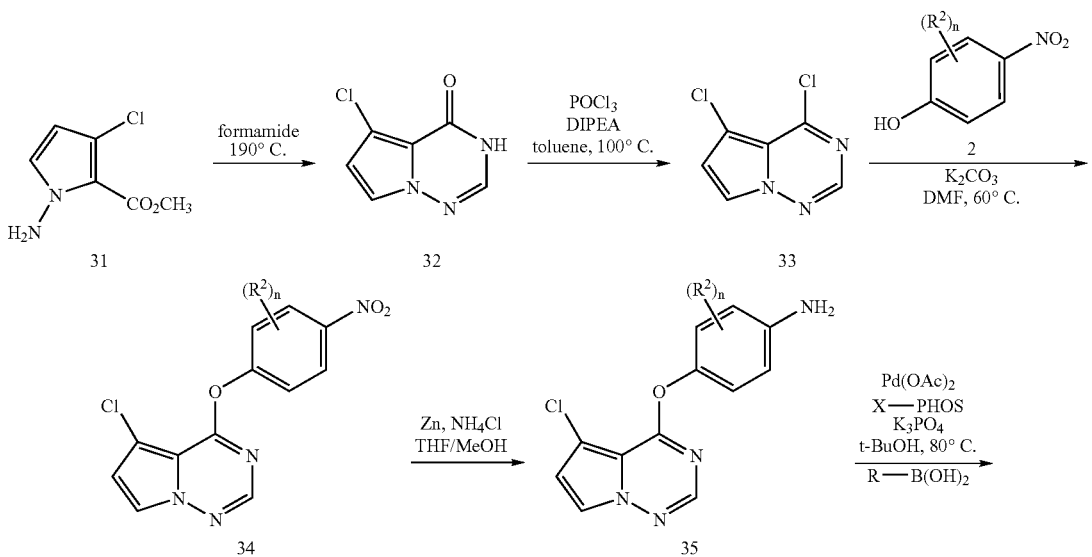

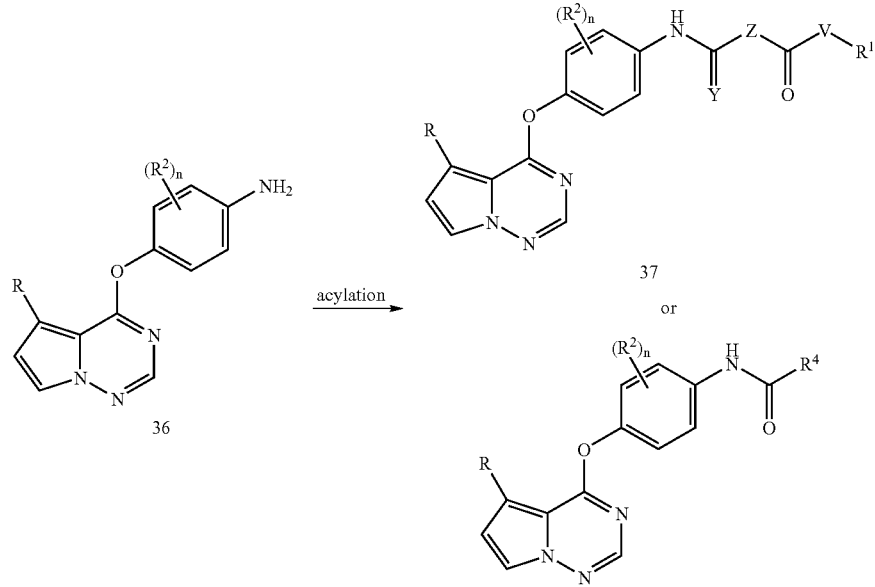

R = aryl, heteroaryl, vinyl

Substitution at the 5-position of the pyrrolo[2,1-f][1,2,4]triazine ring can also be accomplished by coupling the triethylammonium salt 39 with an appropriately substituted phenol 7 followed by treatment with an amine (HNR'R") in the presence of a base, such as Hunig's base to afford the aniline 40 (Scheme 8). Aniline 40 can be further processed as described previously to produce the desired compounds 41 or 42.

SCHEME 8

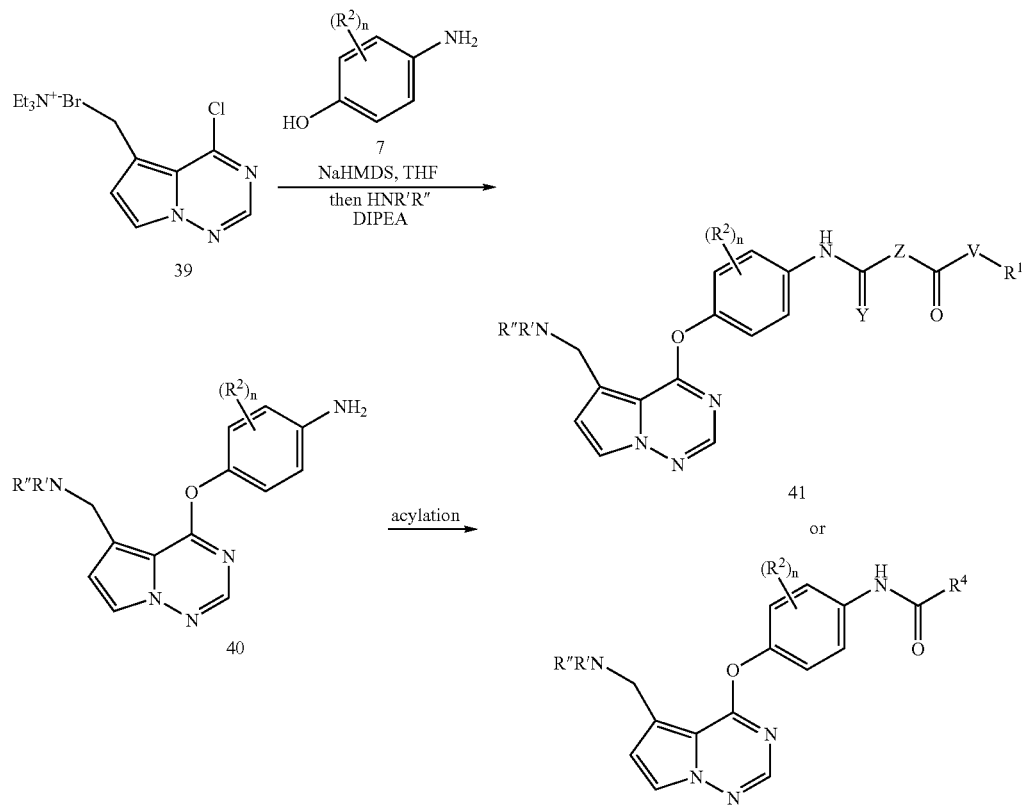

Alternatively, 5-methyl-4-(methylthio)pyrrolo[2,1-f][1,2,4]triazine (43) can be brominated with, for example N-bromosuccinimide (NBS) and 2,2'-azobisisobutyronitrile (AIBN) in carbontetrachloride at elevated temperatures (Scheme 9). Treatment of the bromide intermediate with an amine (HNR'R") in the presence of a base, such as Hunig's base can provide intermediate 44. Oxidation of the thiomethyl group of 44 can be accomplished with, for example 3-chloroperbenzoic acid (m-CPBA). Treatment of the sulfone intermediate with the phenoxide generated from compound 7 and sodium bis(trimethylsilyl)amide (NaHMDS) can provide the aniline intermediate 45.

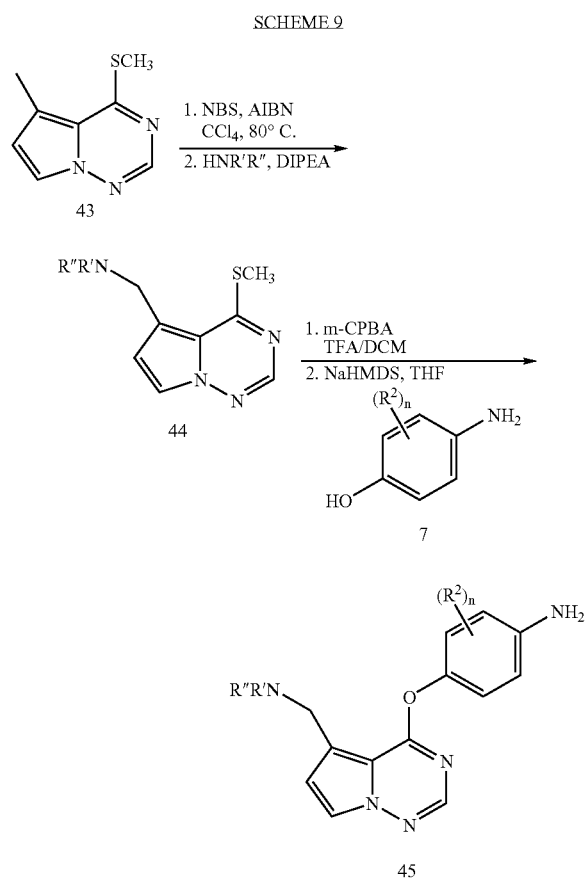

The pyrrolo[2,3-b]pyridine intermediate 50 can be prepared using chemistry outlined in Scheme 10. 4-Chloro-1H-pyrrolo[2,3-b]pyridine (49) can be obtained from commercially available 1H-pyrrolo[2,3-b]pyridine (46) using the synthetic sequence described by Thibault C. and coworkers (*Org. Lett.* 2003, 5, 5023-5025) which is illustrated in Scheme 10. Treatment of intermediate 49 with the phenol 2 at elevated temperatures can afford the key intermediate 50, which can be converted to the desired compounds using chemistry described in Schemes 1 and 3.

The following examples and preparations describe the manner and process of making and using the invention and are illustrative rather than limiting. It should be understood that there may be other embodiments which fall within the spirit and scope of the invention as defined by the claims appended hereto.

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: %0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using $H_2O$/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT: room temperature; $t_R$: retention time; h: hour(s); min: minute(s); PyBrOP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt: hydroxybenzotriazole; HATU: O-(7-azabenzotriazol-1-yl)-N,N,N',N'-tetramethyluronium hexafluorophosphate; DIBAL-H: diisobutylaluminum hydride; Na(OAc)$_3$BH: sodium triacetoxyborohydride; HOAc: acetic acid; TFA: trifluoroacetic acid; LiHMDS: lithium bis(trimethylsilyl)amide; m-CPBA: m-chloro: 3-chloroperbenzoic acid; AIBN: 2,2'-azobisisobutyronitrile; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether.

Example 1

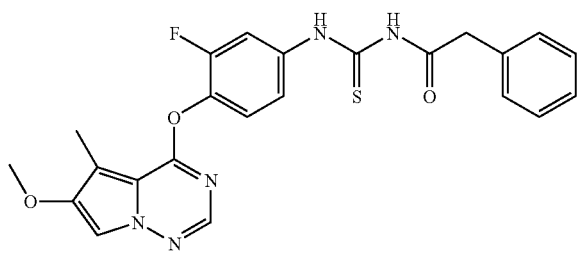

1-(3-Fluoro-4-(6-methoxy-5-methylpyrrolo[2,1-f][1,2,4]triazin-4-yloxy)phenyl)-3-(2-phenylacetyl)thiourea

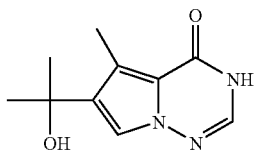

A) 6-(1-Hydroxy-1-methyl-ethyl)-5-methyl-3H-pyrrolo[2,1-f]1,2,4]triazin-4-one

A mixture of 1.9 kg of 5-methyl-4-oxo-3,4-dihydro-pyrrolo[2,1-f][1,2,4]triazine-6-carboxylic acid ethyl ester, prepared generally according to the procedures described in, U.S. patent application Ser. No. 09/573829, and 17.9 kg of THF was prepared under an inert atmosphere and cooled to −10° C. To this mixture was added 14.2 kg methylmagnesium chloride as a 3 M solution in THF at a rate to maintain the reaction temperature <35° C. The reaction mixture was held at 25-45° C. until complete, then cooled to 0° C. A solution of 9.9 kg ammonium chloride in 36.7 kg water was prepared and cooled to 5° C. The organic reaction mixture was added to the ammonium chloride solution at a rate to maintain the internal temperature <15° C. The phases were allowed to settle and the lower aqueous phase drained off and re-extracted with 9.5 kg additional THF. To the combined organic phases was added 8.6 kg EtOAc and the mixture washed with 7.6 kg of saturated aqueous sodium chloride solution. The reaction mixture was filtered, then solvent was removed in vacuo (temperature <40° C.) to about ⅓ the original volume. Additional EtOAc was added with continuing distillation until the THF level was <7%. The resulting slurry was cooled to 0-5° C., then the solid collected by filtration. The wet cake was washed with cold (−10° C.) EtOAc, then dried in vacuo at 40° C. to produce 1.5 kg 6-(1-hydroxy-1-methyl-ethyl)-5-methyl-3H-pyrrolo[2,1-f]1,2,4]triazin-4-one with a purity of 96-99%.

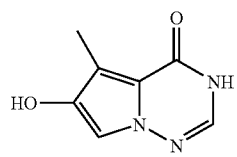

B) 6-Hydroxy-5-methyl-3H-pyrrolo[2,1-f][1,2,4]triazin-4-one

A one liter, 3-neck, round bottom flask as equipped with mechanical stirrer and a cooling bath of ice/acetone. To this was charged 20 g of 6-(1-hydroxy-1-methyl-ethyl)-5-methyl-3H-pyrrolo[2,1-f][1,2,4]triazin-4-one, 235 mL of THF and 47 mL 50% aqueous hydrogen peroxide. An exotherm from −7° C. to 7.3° C. was observed and the mixture became a solution. To this was added a pre-cooled solution of 28.5 mL water and 63 mL methanesulfonic acid over 40 min, keeping the temperature between −5° C. and −0.7° C. The solution was stirred at −2° C. for 95 min until HPLC indicated reaction was complete; reaction mixture was quenched, while keeping it at −2° C., by adding it portion wise to a cooled solution of 28.5 mL water, 89 g NaHSO$_3$ and 128 mL 28% aqueous ammonium hydroxide over 40 min, at 15° C. to 25° C. The mixture was stirred at room temperature for 20 min; pH was 6.80 and a peroxide test was negative. The layers were separated and the aqueous layer was extracted with 100 mL THF. The two organic layers were combined and concentrated, removing 280 mL solvent. To the thick slurry was added 250 mL water and the concentration continued until 88 mL of solvent was removed. The slurry was filtered and the cake was washed with 25 mL water twice and then 25 mL acetonitrile. It was dried by suction on the filter to constant weight to yield 12.51 g of 6-hydroxy-5-methyl-3H-pyrrolo[2,1-f][1,2,4]triazin-4-one, 75.9% yield, 96.5% purity.

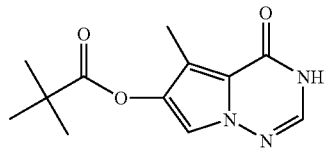

C) 2,2-Dimethyl-propionic acid 5-methyl-4-oxo-3,4-dihydro-pyrrolo[2,1-f][1,2,4]triazin-6-yl ester A mixture of 2.9 kg 6-hydroxy-5-methyl-3H-pyrrolo[2,1-f][1,2,4]triazin-4-one, 4.6 kg of diisopropylethylamine and 17.0 kg of THF was cooled to 0-10° C., then treated with 2.6 kg pivaloyl chloride at a rate to maintain the temperature <20° C. The mixture was stirred until the reaction was complete by HPLC, then 17.8 kg of toluene was added, followed by 20.6 kg of 15% aqueous potassium dihydrogen phosphate solution. The phases were separated and the organic was washed with 10.2 kg water. The organic phase was filtered, then distilled under vacuum with a maximum temperature of 65° C. Additional toluene can be added and distillation continued until the concentration of THF was <8%, and the total reactor volume was reduced to 31 L. The resulting slurry was cooled to 20-25° C. and treated with 20.3 kg heptane over 1.5 h. The slurry was cooled to 0-5° C. and held for 1 h, then the solid was collected by filtration and dried to yield 4.0 kg of 2,2-dimethyl-propionic acid 5-methyl-4-oxo-3,4-dihydro-pyrrolo[2,1-f][1,2,4]triazin-6-yl ester with a purity of 95-99%.

D) 4-Chloro-5-methylpyrrolo[2,1-f][1,2,4]triazin-6-yl pivalate

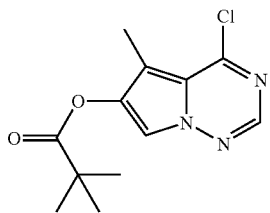

To a mixture of 5-methyl-4-oxo-3,4-dihydropyrrolo[2,1-f][1,2,4]triazin-6-yl pivalate (300 mg, 1.20 mmol), phosphorus oxychloride (368 mg mL, 2.4 mmol) and DIEA (0.5 mL, 2.80 mmol) was added acetonitrile (10 mL). The reaction was heated at 85-90° C. for 4 hours and then cooled to room temperature. The mixture was diluted with ethyl acetate (10 mL) and water (5 mL). The organic layer was separated and dried with sodium sulfate, concentrated in vacuo and purified by silica gel flash chromatography (eluted with 1-25% EtOAc/$CH_2Cl_2$) to give the title compound (250 mg, 78%) as a white solid.

E) 4-(2-Fluoro-4-nitrophenoxy)-5-methylpyrrolo[2,1-f][1,2,4]triazin-6-yl pivalate

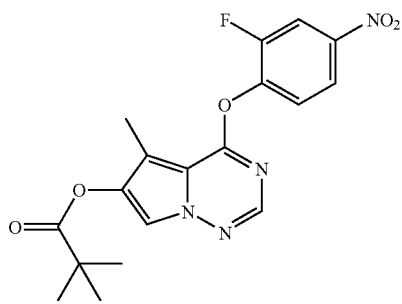

To a mixture 4-chloro-5-methylpyrrolo[2,1-f][1,2,4]triazin-6-yl pivalate (250 mg, 0.94 mmol), 2-fluoro-4-nitrophenol (176 mg, 1.12 mmol, Aldrich) and $K_2CO_3$ (154 mg, 1.12 mmol) was added DMF (5 mL). The reaction was stirred at room temperature for 24 h. The reaction was quenched with water (5 mL) and $CH_2Cl_2$ (10 mL). The organic layer was separated, dried with sodium sulfate, concentrated in vacuo, and purified by silica gel flash chromatography (eluted with 1-25% EtOAc/$CH_2Cl_2$) to give the title compound (160 mg, 44%) as a white solid.

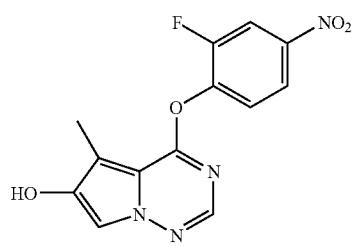

F) 4-(2-Fluoro-4-nitrophenoxy)-5-methylpyrrolo[2,1-f][1,2,4]triazin-6-ol

To a solution of 4-(2-fluoro-4-nitrophenoxy)-5-methylpyrrolo[2,1-f][1,2,4]triazin-6-yl pivalate (80 mg, 0.2 mmol) in THF (1 mL) was added a solution of NaOH in MeOH/$H_2O$ (0.2 mL, 1 M). The solution turned red instantly. After 5 minutes, the reaction was quenched with EtOAc (5 mL) and $H_2O$ (5 mL). The organic layer was separated, dried with sodium sulfate and concentrated in vacuo to give the title compound (52 mg, 85%) as a yellow solid.

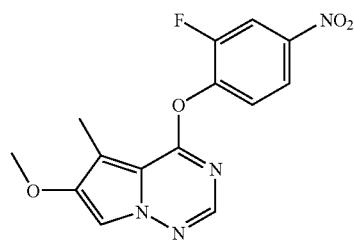

G) 4-(2-Fluoro-4-nitrophenoxy)-6-methoxy-5-methylpyrrolo[2,1-f][1,2,4]triazine To a solution of 4-(2-fluoro-4-nitrophenoxy)-5-methylpyrrolo[2,1-f][1,2,4]triazin-6-ol (52 mg, 0.17 mmol) in DMF (2 mL) was added $Cs_2CO_3$ (65 mg, 0.2 mmol) and the mixture was stirred at RT for 10 minutes. A solution of methyl iodide in DMF (0.2 mL, 0.2 mmol, 1 M) was added and the reaction solution was stirred at RT for 2 h. The reaction was quenched with EtOAc (5 mL) and $H_2O$ (5 mL). The organic layer was separated, dried with sodium sulfate and concentrated in vacuo to give the title compound (35 mg, 65%) as a yellow solid.

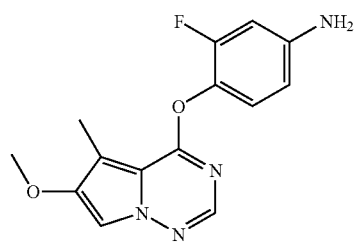

H) 3-Fluoro-4-(6-methoxy-5-methylpyrrolo[2,1-f][1,2,4]triazin-4-yloxy)benzenamine To a solution of 4-(2-fluoro-4-nitrophenoxy)-6-methoxy-5-methylpyrrolo[2,1-f][1,2,4]triazine (35 mg, 0.11 mmol) in THF (1.0 mL) was added MeOH (1.0 mL) followed by Zn (100 mg, 1.5 mmol) and $NH_4Cl$ (43 mg, 0.80 mmol). The reaction was heated at 60° C. for 3 h. The solution was filtered through Celite® and concentrated in vacuo. The product mixture was purified by a SCX cartridge (eluted with ammonia in methanol (2 M) to give the title compound (15 mg, 50%) as a white solid.

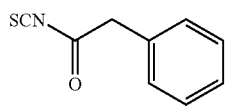

I) 2-Phenyl-1-thiocyanatoethanone

To a solution of NaSCN (49 mg, 0.60 mmol) in EtOAc (2 mL) was added phenylacetyl chloride (0.066 mL, 0;50 mmol, Aldrich) to provide a 0.25 M solution of 2-phenyl-1-thiocyanatoethanone. After 10 min, completion of the reaction was determined by reacting an aliquot of the reaction mixture with 4-(phenyloxy)aniline to form the corresponding thiocyanate which was detected by LCMS(ESI$^+$) m/z 363 (M+H)$^+$. The 2-phenyl-1-thiocyanatoethanone was used directly without isolation or farther purification.

J) 1-(3-Fluoro-4-(6-methoxy-5-methylpyrrolo[2,1-f][1,2,4]triazin-4-yloxy)phenyl)-3-(2-phenylacetyl)thiourea To a solution of 3-fluoro-4-(6-methoxy-5-methylpyrrolo[2,1-f][1,2,4]triazin-4-yloxy)benzenamine (7.5 mg, 0.026 mmol) in CH$_2$Cl$_2$ (1 mL) was added a solution of 2-phenyl-1-thiocyanatoethanone (0.133 mL, 0.033 mmol, 0.25 M in ethyl acetate). The reaction was stirred at room temperature for 20 minutes, concentrated in vacuo and purified by silica gel flash chromatography (eluted with 1-25% EtOAc/CH$_2$Cl$_2$) to give the title compound (6.1 mg, 50%) as a pale yellow solid. $^1$H NMR (CDCl$_3$) δ 8.51 (s, 1H), 7.87 (m, 1H), 7.83 (s, 1H), 7.47 (m, 5H), 7.31 (m, 4H), 3.89 (s, 3H), 3.74 (d, 2H, J=10.5 Hz), 2.44 (s, 3H); MS(ESI$^+$) m/z 466 (M+H)$^+$.

Example 2

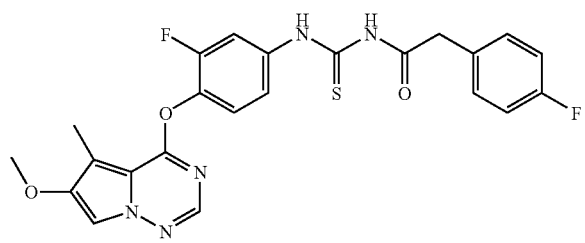

1-(3-Fluoro-4-(6-methoxy-5-methylpyrrolo[2,1-f][1,2,4]triazin-4-yloxy)phenyl)-3-(2-(4-fluorophenyl)acetyl)thiourea

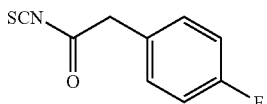

A) 2-(4-Fluorophenyl)-1-thiocyanatoethanone

To a solution of NaSCN (49 mg, 0.60 mmol) in EtOAc (2 mL) was added 4-fluorophenylacetyl chloride (0.066 mL, 0.50 mmol, Aldrich). The reaction was stirred at room temperature for 1 h to give a 0.25 M solution of 2-(4-fluorophenyl)-1-thiocyanatoethanone in EtOAc, which was used directly without further purification.

B) 1-(3-Fluoro-4-(6-methoxy-5-methylpyrrolo[2,1-f][1,2,4]triazin-4-yloxy)phenyl)-3-(2-(4-fluorophenyl)acetyl)thiourea The title compound was prepared from 3-fluoro-4-(6-methoxy-5-methylpyrrolo[2,1-f][1,2,4]triazin-4-yloxy)benzenamine and 2-(4-fluorophenyl)-1-thiocyanatoethanone in a similar manner as described for Compounds H and J of Example 1. $^1$H NMR (CDCl$_3$) δ 8.49 (s, 1H), 7.88 (m, 1H), 7.83 (s, 1H), 7.45 (s, 1H), 7.28 (m, 5H), 7.12 (m, 2H), 3.89 (s, 3H), 3.71 (s, 2H) 2.44 (s, 3H); MS(ESI$^+$) m/z 484 (M+H)$^+$.

Example 3

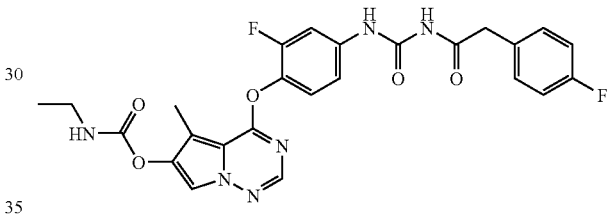

4-(2-Fluoro-4-(3-(2-(4-fluorophenyl)acetyl)ureido)phenoxy)-5-methylpyrrolo[2,1-f][1,2,4]triazin-6-yl ethylcarbamate

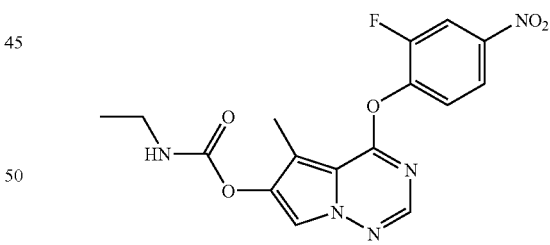

A) 4-(2-Fluoro-4-nitrophenoxy)-5-methylpyrrolo[2,1-f][1,2,4]triazin-6-yl ethylcarbamate To a mixture of 4-(2-fluoro-4-nitrophenoxy)-5-methylpyrrolo[2,1-f][1,2,4]triazin-6-ol (25 mg, 0.082 mmol, Compound F of Example 1), DIEA (0.017 mL, 0.1 mmol) in CH$_2$Cl$_2$ (5 mL) was added ethyl isocyanate (0.078 mL, 0.1 mL) and stirred at room temperature for 2 h. The reaction was quenched with water (5 mL). The organic layer was separated, dried and concentrated in vacuo. The mixture was purified by flash chromatography (1-5% Methanol/CH$_2$Cl$_2$) to give the title compound (12.5 mg, 32%) as a white solid.

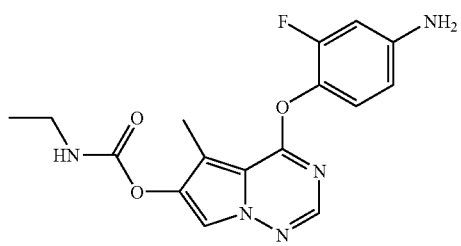

B) 4-(4-Amino-2-fluorophenoxy)-5-methylpyrrolo[2,1-f][1,2,4]triazin-6-yl ethylcarbamate To a solution of 4-(2-fluoro-4-nitrophenoxy)-5-methylpyrrolo[2,1-f][1,2,4]triazin-6-yl ethylcarbamate (12.5 mg, 0.033 mmol) in ethanol (2 mL) was added Zn (20 mg, 0.3 mmol) and NH$_4$Cl (20 mg, 0.37 mmol). The reaction was stirred at room temperature for 1 h, filtered through Celite® and concentrated in vacuo to give the title compound (8 mg, 70%) as a white solid.

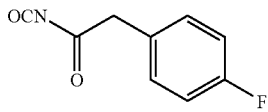

C) 2-(4-Fluorophenyl)acetyl isocyanate

To a solution/suspension of 4-fluorophenylacetamide (77 mg, 0.50 mmol, see generally, *J. Med. Chem.* 2003, 46, 4333-4341, the disclosure of which is herein incorporated by referene) in dichloroethane (2 mL) was added oxalyl chloride (0.175 mL, 2.00 mmol). The reaction was heated at 80° C. for 24 h and then 70° C. for two days. By this time, most of the solids had dissolved and the reaction was yellow. LC/MS analysis found a peak with a molecular weight of 211 corresponding to methyl 2-(4-fluorophenyl)acetylcarbamate, resulting from quenching of the isocyanate with methanol. The reaction was concentrated in vacuo to give a yellow slurry. The slurry was redissolved in dichloroethane (2 mL) and again concentrated in vacuo. The resulting residue was redissolved again in dichloroethane (2 mL) to give a 0.25 M solution of 2-(4-fluorophenyl)acetyl isocyanate in dichloroethane, which was used directly in subsequent reactions.

D) 4-(2-Fluoro-4-(3-(2-(4-fluorophenyl)acetyl)ureido)phenoxy)-5-methylpyrrolo[2,1-f][1,2,4]triazin-6-yl ethylcarbamate To a solution of 4-(4-amino-2-fluorophenoxy)-5-methylpyrrolo[2,1-f][1,2,4]triazin-6-yl ethylcarbamate (10 mg, 0.029 mmol) in CH$_2$Cl$_2$ (1 mL) was added a solution of 2-(4-fluorophenyl)acetyl isocyanate (2 mL, 0.25 M in dichloroethane). The reaction was stirred at room temperature for 1 h, LC/MS analysis indicated consumption of starting carbamate. The mixture was concentrated in vacuo and the residue was suspended in methanol and filtered to give the title compound. The filtrate was purified by flash chromatography to provide more of the title compound as a pale yellow solid (combined yield 5.9 mg, 40%). $^1$H NMR (CDCl$_3$) δ10.63 (s, 1H), 8.42 (s, 1H), 7.88 (s, 1H), 7.82 (s, 1H), 7.67 (dd, 1H, J=12.1, 2.2 Hz), 7.28 (m, 4H), 7.10 (m, 2H), 3.73 (s, 3H), 3.36 (m, 2H), 2.48 (s, 3H), 1.26 (m, 3H); MS(ESI$^+$) m/z 525 (M+H)$^+$.

Example 4

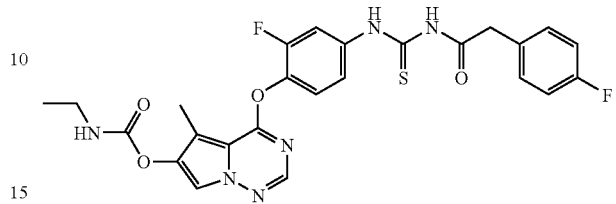

4-(2-Fluoro-4-(3-(2-(4-fluorophenyl)acetyl)thioureido)phenoxy)-5-methylpyrrolo[2,1-f][1,2,4]triazin-6-yl ethylcarbamate To a solution of 4-(4-amino-2-fluorophenoxy)-5-methylpyrrolo[2,1-f][1,2,4]triazin-6-yl ethylcarbamate (8 mg, 0.023 mmol, preparation Compound B of Example 4) in CH$_2$Cl$_2$ (1 mL) was added a solution of 2-(4-fluorophenyl)-1-thiocyanatoethanone (0.120 mL, 0.025 mmol, 0.25 M in ethyl acetate, Compound A of Example 2). The reaction was stirred at room temperature for 1 h, concentrated in vacuo and purified by silica gel flash chromatography (eluted with 1-25% EtOAc/CH$_2$Cl$_2$) to give the title compound (5.4 mg, 43%) as a pale yellow solid. $^1$H NMR (CDCl$_3$) δ12.41 (s, 1H), 8.58 (s, 1H), 7.88 (m, 3H), 7.28 (m, 5H), 7.12 (m, 2H), 3.72 (s, 2H), 3.37 (m, 2H), 2.46 (m, 3H), 1.26 (m, 3H); MS(ESI$^+$) m/z 541 (M+H)$^+$.

Example 5

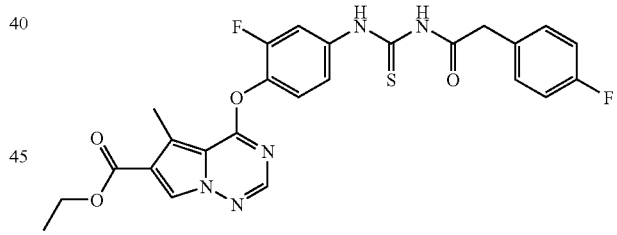

Ethyl 4-(2-fluoro-4-(3-(2-(4-fluorophenyl)acetyl)thioureido)phenoxy)-5-methylpyrrolo[2,1-f][1,2,4]triazine-6-carboxylate

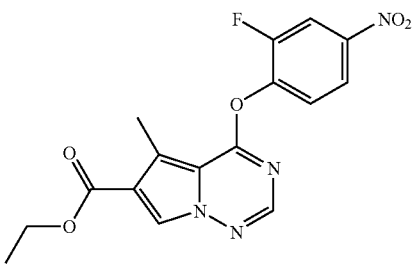

A) Ethyl 4-(2-fluoro-4-nitrophenoxy)-5-methylpyrrolo[2,1-f][1,2,4]triazine-6-carboxylate To a mixture of ethyl 4-chloro-5-methylpyrrolo[2,1-f][1,2,4]triazine-6-carboxylate (24 mg, 0.10 mmol, preparation: See, U.S. Pat. No. 6,670,357, especially example 61, the disclosure of which is hererin incorporated by reference), 2-fluoro-4-nitrophenol (20 mg, 0.125 mmol) and K₂CO₃ (28 mg, 0.20 mmol) was added DMF (0.5 mL). The reaction was heated at 70° C. for 20 minutes, cooled to room temperature and 2 mL of water was added. The mixture was filtered, the solid was washed with water, and dried to give the title compound (36 mg, 100%) as a light yellow solid.

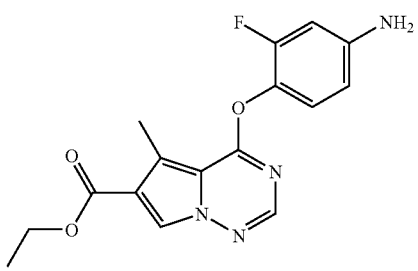

B) Ethyl 4-(4-amino-2-fluorophenoxy)-5-methylpyrrolo[2,1-f][1,2,4]triazine-6-carboxylate To a solution of ethyl 4-(2-fluoro-4-nitrophenoxy)-5-methylpyrrolo[2,1-f][1,2,4]triazine-6-carboxylate (36 mg, 0.1 mmol) in THF (1.0 mL) was added MeOH (0.7 mL) followed by Zn (130 mg, 2.0 mmol) and NH₄Cl (53 mg, 1.0 mmol). The reaction was heated at 70° C. overnight. LC/MS analysis indicated mostly starting material. The solution was shaken vigorously and then heated to 75° C. LC/MS analysis after 4 h showed the desired product and many other peaks. The reaction was filtered through a coarse filter, and the filtrate was concentrated to a give 55 mg of a brown residue. The residue was suspended in THF and passed through an HPLC filter resulting in a clear filtrate. The filtrate was concentrated in vacuo to give 54 mg of the title compound as a crude mixture which was used in the next step without further purification.

C) Ethyl 4-(2-fluoro-4-(3-(2-(4-fluorophenyl)acetyl)thioureido)phenoxy)-5-methylpyrrolo[2,1-f][1,2,4]triazine-6-carboxylate To a suspension of ethyl 4-(4-amino-2-fluorophenoxy)-5-methylpyrrolo[2,1-f][1,2,4]triazine-6-carboxylate (54 mg) in CH₂Cl₂ (0.6 mL) was added a solution of 2-(4-fluorophenyl)-1-thiocyanatoethanone (0.5 mL, 0.12 mmol, 0.25 M in ethyl acetate Compound A of Example 2). The reaction was stirred at room temperature for 15 minutes, LC/MS analysis indicated mostly starting material. The reaction was warmed to 45° C., after 30 min most of the suspension had dissolved to give a cloudy solution. LC/MS analysis indicated mostly desired product. The reaction was shaken at room temperature for an additional 2 h, evaporated to dryness, and purified by column chromatography eluting with 1-7% ethyl acetate/dichloromethane to the title compound (9 mg, 17% overall yield for 3 steps) as a white solid. ¹H NMR (CDCl₃) δ 12.45 (s, 1H), 8.66 (s, 1H), 8.18 (s, 1H), 7.92 (dd, 1H, J=11.4, 2.4 Hz), 7.90 (s, 1H), 7.41 (m, 1H), 7.29 (m, 3H), 7.12 (m, 2H), 4.38 (q, 2H, J=7.1 Hz), 3.73 (s, 2H), 2.82 (s, 3H), 1.40 (t, 3H, J=7.1 Hz); MS(ESI⁺) m/z 526 (M+H)⁺.

Example 6

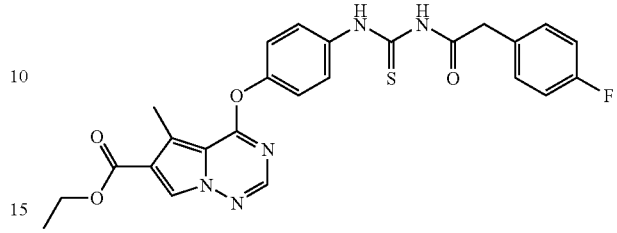

Ethyl 4-(4-(3-(2-(4-fluorophenyl)acetyl)thioureido)phenoxy)-5-methylpyrrolo[2,1-f][1,2,4]triazine-6-carboxylate

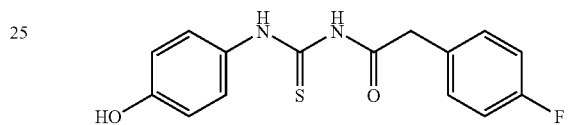

A) 1-(2-(4-Fluorophenyl)acetyl)-3-(4-hydroxyphenyl)thiourea

To a solution of 4-amino-phenol (11 mg, 0.1 mmol, Aldrich) in CH₂Cl₂ (0.55 mL) was added a solution of 2-(4-fluorophenyl)-1-thiocyanatoethanone (0.5 mL, 0.125 mmol, 0.25 M in ethyl acetate, Compound A of Example 2). The reaction was stirred at room temperature for 10 minutes, LC/MS analysis indicated formation of the title compound. The crude reaction mixture was used directly in the next reaction.

B) Ethyl 4-(4-(3-(2-(4-fluorophenyl)acetyl)thioureido)phenoxy)-5-methylpyrrolo[2,1-f][1,2,4]triazine-6-carboxylate To a room temperature solution of ethyl 4-chloro-5-methylpyrrolo[2,1-f][1,2,4]triazine-6-carboxylate (7.2 mg, 0.03 mmol) (for preparation see U.S. Pat. No. 6,670,357, the disclosure of which is herein incorporated by reference) and DABCO (7 mg, 0.06 mmol) in acetonitrile (0.5 mL) was added 1-(2-(4-fluorophenyl)acetyl)-3-(4-hydroxyphenyl)thiourea (0.5 mL, 0.05 mmol). The reaction was shaken at room temperature. After 30 min, LC/MS analysis indicated mostly product. The reaction was stirred at room temperature overnight. The mixture was evaporated to dryness. Purification by silica gel chromatography (eluting with 1% methanol/dichloromethane) provided the desired product contaminated with impurities. A second purification by silica gel chromatography (1-6% Ethyl acetate/dichloromethane) again did not remove all of the impurities. The resulting solid mixture was washed with methanol and dried to provide the title compound (6 mg, 39%) as a yellow solid. ¹H NMR (CDCl₃) δ 12.32 (s, 1H), 8.62 (s, 1H), 8.16 (s, 1H), 7.91 (s, 1H), 7.76 (m, 2H), 7.29 (m, 4H), 7.12 (m, 2H), 4.38 (q, 2H, J=7.1 Hz), 3.72 (s, 2H), 2.82 (s, 3H), 1.40 (t, 3H, J=7.1 Hz); MS(ESI⁺) m/z 508 (M+H)⁺.

Example 7

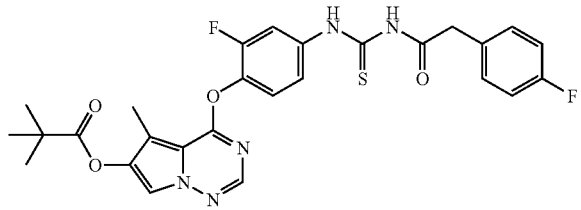

4-(2-Fluoro-4-(3-(2-(4-fluorophenyl)acetyl)thioure-
ido)phenoxy)-5-methylpyrrolo[2,1-f][1,2,4]triazin-6-
yl pivalate To a mixture of 1-(3-fluoro-4-hydroxyphenyl)-3-(2-(4-fluorophenyl)acetyl)thiourea (60 mg, 0.19 mmol, Compound A of Example 3), 4-chloro-5-methylpyrrolo[2,1-f][1,2,4]triazin-6-yl pivalate (50 mg, 0.19 mmol, Compound D of Example 1) and 1,4-diazabicyclo[2.2.2]octane (DABCO, 21.3 mg, 0.19 mmol) was added MeCN (5 mL). The reaction was stirred at RT for 1 h and concentrated in vacuo. The residue was purified by flash chromatography (eluted with 1-15% MeOH/CH$_2$Cl$_2$) to give the title compound (91 mg, 86%) as a white solid. $^1$H NMR (CDCl$_3$) δ12.40 (s, 1H), 8.54 (s, 1H), 7.87 (m, 3H), 7.29 (m, 4H), 7.12 (m, 2H), 3.71 (s, 2H), 2.43 (s, 3H), 1.39 (s, 9H); MS(ESI$^+$) m/z 554 (M+H)$^+$.

Example 8

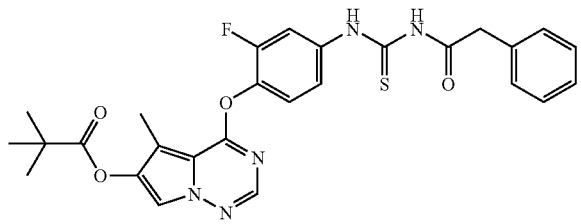

4-(2-Fluoro-4-(3-(2-phenylacetyl)thioureido)phe-
noxy)-5-methylpyrrolo[2,1-f][1,2,4]triazin-6-yl piv-
alate

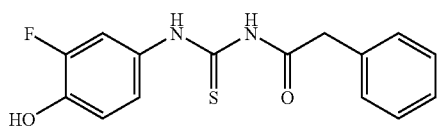

A) 1-(3-Fluoro-4-hydroxyphenyl)-3-(2-phenylacetyl)
thiourea

To a solution of 4-amino-3-fluorophenol (50 mg, 0.3 mmol) in CH$_2$Cl$_2$ (2 mL) was added a solution of 2-phenyl-1-thiocyanatoethanone (2 mL, 0.4 mmol, 0.2 M in ethyl acetate, Compound I of Example 1). The reaction was stirred at room temperature for 20 minutes, LC/MS analysis indicated formation of the title compound. The mixture was concentrated to give a residue that was used without further purification.

B) 4-(2-Fluoro-4-(3-(2-phenylacetyl)thioureido)phe-
noxy)-5-methylpyrrolo[2,1-f][1,2,4]triazin-6-yl piv-
alate A vial was charged with 4-chloro-5-methylpyrrolo[2,1-f][1,2,4]triazin-6-yl pivalate (13.3 mg, 0.19 mmol, Compound D of Example 1), 1-(3-fluoro-4-hydroxyphenyl)-3-(2-phenylacetyl)thiourea (16 mg, 0.05 mmol), cesium carbonate (spatula tip) and DMF (2 mL) and warmed to 100° C. for 26 h. The mixture was concentrated in vacuo. The residue was purified by flash chromatography to give the title compound (6.2 mg, 25%) as a white solid. $^1$H NMR (CDCl$_3$) δ12.46 (s, 1H), 8.50 (s, 1H), 7.88 (m, 3H), 7.40 (m, 4H), 7.31 (m, 2H), 3.75 (s, 3H), 2.44 (s, 3H), 1.40 (s, 9H); MS(ESI$^+$) m/z 536 (M+H)$^+$.

What is claimed is:

1. A process for making a compound having the formula VI:

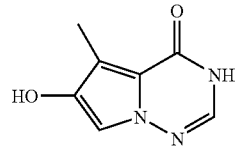

comprising contacting a compound having formula V

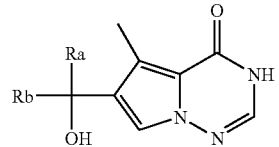

wherein R$^a$ and R$^b$ are alkyl, with an acid in the presence of a peroxide for a time and under conditions sufficient to produce compound VI.

2. The process of claim 1 wherein said acid is an organic acid, a mineral acid, a Lewis acid, or an acidic ion exchange resin.

3. The process of claim 1 wherein said acid is selected from the group consisting of p-toluene sulfonic acid, methanesulfonic acid, BF$_3$-OEt, trifluoroacetic acid, formic acid, sulfuric acid, nitric acid, an acidic zeolite, and an acidic ion exchange resin.

4. The process of claim 1 wherein the concentration of said peroxide ranges from about 30% to about 90%.

5. The process of claim 1 wherein the concentration of said peroxide ranges from about 30% to about 50%.

6. The process of claim 1 further comprising the step of quenching the reaction with the addition of a reducing agent.

7. The process of claim 6 wherein said reducing agent is sodium metabisulfite, sodium hydrogen sulfite, sodium thiosulfate, or sodium hydrogen sulfite.

8. A method of preparing a compound of formula VII:

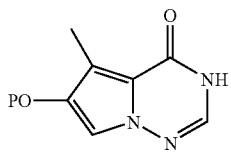

VII wherein P is a protecting group, comprising the step of contacting a compound having formula VI:

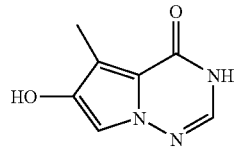

VI with an acylating or an alkylating agent for a time and under conditions to effect an acylation or an alkylation reaction that yields compound VII.

9. The method of claim 8 wherein said acylation agent is formic acid, acetyl chloride, acetic anhydride, pivaloyl chloride, pivalic anhydride, benzoyl chloride, di-t-butyl dicarbonate and said alkylation agent is selected from the group consisting of methyl iodide, methyl bromide, dimethylsulfate, dimethyl carbonate, chloromethylmethyl ether, 3,4-dihydro-2H-pyran, benzyl chloride, benzyl bromide, 4-methoxybenzylchloride, 4-methoxybenzyl bromide.

* * * * *